United States Patent
Chen et al.

(10) Patent No.: US 9,968,530 B2
(45) Date of Patent: *May 15, 2018

(54) CLEANSING COMPOSITION

(71) Applicant: KAO CORPORATION, Chuo-ku (JP)

(72) Inventors: Jenru Chen, Tsukuba (JP); Naoko Yamamoto, Sumida-ku (JP); Atsushi Tomokuni, Shinagawa-ku (JP)

(73) Assignee: KAO CORPORATION, Chuo-ku (JP)

(*) Notice: Subject to any disclaimer, the term of this patent is extended or adjusted under 35 U.S.C. 154(b) by 0 days. days.

This patent is subject to a terminal disclaimer.

(21) Appl. No.: 14/655,234

(22) PCT Filed: Dec. 27, 2013

(86) PCT No.: PCT/JP2013/085231
§ 371 (c)(1),
(2) Date: Jun. 24, 2015

(87) PCT Pub. No.: WO2014/104349
PCT Pub. Date: Jul. 3, 2014

(65) Prior Publication Data
US 2015/0328127 A1    Nov. 19, 2015

(30) Foreign Application Priority Data

Dec. 28, 2012  (JP) .................................. 2012-289108
Jul. 31, 2013   (JP) .................................. 2013-159805
Jul. 31, 2013   (JP) .................................. 2013-159807

(51) Int. Cl.

| | | |
|---|---|---|
| C11D 3/18 | (2006.01) | |
| C11D 3/20 | (2006.01) | |
| A61K 8/31 | (2006.01) | |
| A61K 8/33 | (2006.01) | |
| A61K 8/36 | (2006.01) | |
| A61K 8/81 | (2006.01) | |
| A61Q 1/14 | (2006.01) | |
| A61Q 19/00 | (2006.01) | |
| A61K 8/34 | (2006.01) | |
| A61K 8/73 | (2006.01) | |
| A61K 8/86 | (2006.01) | |

(52) U.S. Cl.
CPC .................. *A61K 8/34* (2013.01); *A61K 8/31* (2013.01); *A61K 8/33* (2013.01); *A61K 8/731* (2013.01); *A61K 8/8147* (2013.01); *A61K 8/8152* (2013.01); *A61K 8/86* (2013.01); *A61Q 1/14* (2013.01); *A61K 2800/594* (2013.01)

(58) Field of Classification Search
CPC ........... C11D 3/18; C11D 3/20; C11D 3/3757; A61K 8/31; A61K 8/33; A61K 8/36; A61K 8/81; A61Q 1/14; A61Q 19/00
See application file for complete search history.

(56) References Cited

U.S. PATENT DOCUMENTS

| | | | |
|---|---|---|---|
| 5,585,104 A | 12/1996 | Ha et al. | |
| 8,524,205 B2 | 9/2013 | Oshika et al. | |
| 2012/0263671 A1* | 10/2012 | Okubo | ................. A61K 8/0295 424/78.02 |
| 2012/0294912 A1* | 11/2012 | Fukui | ................... A61K 8/0254 424/401 |
| 2012/0295989 A1* | 11/2012 | Okubo | ..................... A61K 8/31 514/772.6 |

FOREIGN PATENT DOCUMENTS

| | | |
|---|---|---|
| JP | 8-104610 A | 4/1996 |
| JP | 11-503461 A | 3/1999 |
| JP | 2004-175774 A | 6/2004 |
| JP | 2004-339212 A | 12/2004 |
| JP | 2007-55925 A | 3/2007 |
| JP | 2009-242340 A | 10/2009 |
| JP | 2010-168293 | 8/2010 |
| JP | 2010-280597 A | 12/2010 |
| JP | 2012-201601 A | 10/2012 |
| JP | 2012-201622 A | 10/2012 |
| JP | 2015-30682 A | 2/2015 |
| JP | 2015-30683 A | 2/2015 |
| JP | 2015-30684 A | 2/2015 |
| WO | 2014/104349 A1 | 7/2014 |
| WO | 2015/016277 A1 | 2/2015 |

OTHER PUBLICATIONS

International Search Report dated Mar. 4, 2014 in PCT/JP13/085231 Filed Dec. 27, 2013.

* cited by examiner

*Primary Examiner* — Brian P Mruk
(74) *Attorney, Agent, or Firm* — Oblon, McClelland, Maier & Neustadt, L.L.P.

(57) ABSTRACT

The present invention provides a cleansing composition comprising the following components (A), (B), and (C): (A) 0.001 to 5% by mass of a polymer selected from the group consisting of (A-1), (A-2), and (A-3): (A-1) an acrylic copolymer comprising 10 mol % or more of a monomer selected from the group consisting of an acrylic acid alkyl ester and a methacrylic acid alkyl ester, as represented by mol % based on the total monomers; (A-2) a polysaccharide derivative having a polyoxyalkylene chain having an average molecular weight of 300 to 100,000; and (A-3) a polyether polycarbonate; (B) 1 to 50% by mass of one or two or more oil agents selected from the group consisting of (b1) and (b2): (b1) an ether oil and (b2) a hydrocarbon oil having a viscosity of 18 mPa·s or lower at 30° C.; and (C) water, and comprising (D) no nonionic surfactant having HLB of 8 or more or less than 5% by mass of the nonionic surfactant.

23 Claims, No Drawings

CLEANSING COMPOSITION

CROSS REFERENCE TO RELATED APPLICATION

This application is a 371 of PCT/JP2013/085231, filed on Dec. 27, 2013, and claims priority to the following Japanese Patent Applications: i) 2012-289108, filed on Dec. 28, 2012; ii) 2013-159805, filed on Jul. 31, 2013; and iii) 2013-159807, filed on Jul. 31, 2013.

FIELD OF THE INVENTION

The present invention relates to a cleansing composition.

BACKGROUND OF THE INVENTION

Combined use of acrylic acid/alkyl methacrylate copolymer with oil has heretofore been studied for cleansing compositions for use in wiping off makeup or for rinsing off makeup (Patent Publications 1 to 3).

Various cleansing agents for removing makeup have been developed according to the diversification of makeup cosmetics or the preference of consumers. In recent years, the number of stay-put waterproof mascara has increased. Thus, cleansing agents which can thoroughly remove even stay-put waterproof mascara have been studied.

For example, Patent Publication 2 describes a cleansing composition comprising a particular water-soluble compound, oil agent, and aqueous thickener. Patent Publication 3 describes a cleansing cosmetic comprising a volatile silicone oil, a volatile hydrocarbon oil, a nonvolatile silicone oil, a hydrophilic nonionic surfactant, an acrylic polymer, and water.

CITATION LIST

Patent Publications (Patent Publication 1) JP-A-hei11-503461
(Patent Publication 2) JP-A-2004-339212
(Patent Publication 3) JP-A-2009-242340

SUMMARY OF INVENTION

The first aspect of the present invention relates to a cleansing composition comprising the following components (A), (B), and (C):
(A) 0.001 to 5% by mass of a polymer selected from the group consisting of (A-1), (A-2), and (A-3):
(A-1) a copolymer comprising monomers selected from the group consisting of (a1), (a2), and (a3) as constitutional units:
(a1) a monomer selected from the group consisting of acrylic acid and methacrylic acid,
(a2) a monomer selected from the group consisting of an acrylic acid alkyl ester and a methacrylic acid alkyl ester, and
(a3) a monomer selected from the group consisting of a polyoxyethylene alkyl ester of acrylic acid and a polyoxyethylene alkyl ester of methacrylic acid, and comprising 10 mol % or more of (a2) as represented by mol % based on the total monomers;
(A-2) a polysaccharide derivative having a polyoxyalkylene chain having an average molecular weight of 300 to 100,000 and having a constitutional unit represented by formula (1):

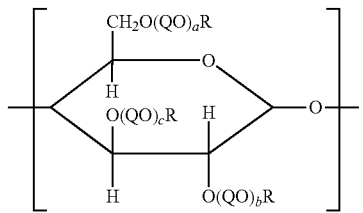

wherein R identically or differently represents a group selected from the group consisting of (d) a hydrogen atom, a methyl group, an ethyl group, a hydroxyethyl group, and a hydroxypropyl group, (e) a substituent comprising a polyoxyalkylene group, (f) a sulfoalkyl group, (g) a carboxyalkyl group, and (h) a cationic substituent; Q identically or differently represents an alkylene group having 2 to 4 carbon atoms; a, b, and c identically or differently represent a number of 0 to 10; the QO groups, the R groups, or the numbers a, b, and c are identical or different in each repeating unit or between repeating units; and when each of the substituents (e) to (h) has a hydroxy group, the hydroxy group is optionally further substituted by any of the other substituents (e) to (h), provided that at least one or more substituents (e) exist as R; and
(A-3) a polyether polycarbonate having a constitutional unit represented by formula (2):

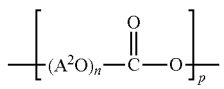

wherein $A^2$ represents an alkylene group having 2 to 6 carbon atoms; n represents a number of 5 to 1,000 on average; p represents a number of 5 to 100 on average; and $A^2$, having a number of (n×p) units, are identical or different;
(B) 1 to 50% by mass of one or two or more oil agents selected from the group consisting of (b1) and (b2):
(b1) an ether oil and
(b2) a hydrocarbon oil having a viscosity of 18 mPa·s or lower at 30° C.; and
(C) water, and
comprising (D) no nonionic surfactant having HLB of 8 or more or less than 5% by mass of the nonionic surfactant.

The second aspect of the present invention relates to a skin cleansing composition comprising the following components (G), (H), (I), and (J):
(G) 0.001 to 5% by mass of a polymer selected from the group consisting of (G-1), (G-2), and (G-3):
(G-1) a copolymer comprising monomers selected from the group consisting of (g1), (g2), and (g3) as constitutional units:
(g1) a monomer selected from the group consisting of acrylic acid and methacrylic acid,
(g2) a monomer selected from the group consisting of an acrylic acid alkyl ester and a methacrylic acid alkyl ester, and
(g3) a monomer selected from the group consisting of a polyoxyethylene alkyl ester of acrylic acid and a polyoxyethylene alkyl ester of methacrylic acid, and comprising 10 mol % or more of the monomer unit (g2) based on the total monomers;

(G-2) a polysaccharide derivative having a polyoxyalkylene chain having an average molecular weight of 300 to 100,000 and having a constitutional unit represented by formula (1):

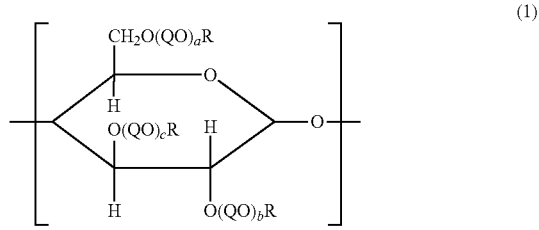

wherein R identically or differently represents a group selected from the group consisting of (d) a hydrogen atom, a methyl group, an ethyl group, a hydroxyethyl group, and a hydroxypropyl group, (e) a substituent comprising a polyoxyalkylene group, (f) a sulfoalkyl group, (g) a carboxyalkyl group, and (h) a cationic substituent; Q identically or differently represents an alkylene group having 2 to 4 carbon atoms; a, b, and c identically or differently represent a number of 0 to 10; the QO groups, the R groups, or the numbers a, b, and c are identical or different in each repeating unit or between repeating units; and when each of the substituents (e) to (h) has a hydroxy group, the hydroxy group is optionally further substituted by any of other substituents (e) to (h), provided that at least one or more substituents (e) exist as R; and (G-3) a polyether polycarbonate having a constitutional unit represented by formula (2):

wherein $A^2$ represents an alkylene group having 2 to 6 carbon atoms; n represents a number of 5 to 1,000 on average; p represents a number of 5 to 100 on average; and $A^2$, having a number of (n×p) units, are identical or different;
(H) 0.001 to 1% by mass of a polymer comprising acrylic acid or methacrylic acid as a constituent, other than the component (G-1);
(I) 0.5 to 30% by mass of a hydrocarbon oil having a viscosity of 18 mPa·s or lower at 30° C.; and
(J) 40 to 98% by mass of water, and comprising (K) no nonionic surfactant or 5% by mass or less of the nonionic surfactant, wherein
the mass ratio between the components (G) and (H), (G)/(H) is 0.1 to 150.

DESCRIPTION OF EMBODIMENTS

Conventional cleansing compositions have an insufficient cleansing power. Another problem of the conventional cleansing compositions is that an oily feeling remains on the skin after wiping or after rinsing.
The present invention relates to a cleansing composition which can thoroughly remove even a stay-put makeup such as waterproof mascara and refreshes the skin after wiping or after rinsing.

The present inventors have found that a cleansing composition which can thoroughly remove even a stay-put makeup such as waterproof mascara and refreshes the skin after wiping or after rinsing can be obtained by using a particular copolymer and a particular oil agent in combination.
The cleansing composition of the present invention produces a high cleansing power for even a stay-put makeup such as waterproof mascara, refreshes the skin after cleansing, and offers a clean feeling.
In the present invention, the clean feeling means that a user feels like nothing remains on the skin by thoroughly removing dirt, feels like the skin has been fully washed, or feels like the skin has become bare skin.
The polymer as the component (A) used in the first aspect of the present invention is selected from the group consisting of (A-1), (A-2), and (A-3).
(A-1) A copolymer comprising monomers selected from the group consisting of (a1), (a2), and (a3) as constitutional units:
(a1) a monomer selected from the group consisting of acrylic acid and methacrylic acid,
(a2) a monomer selected from the group consisting of an acrylic acid alkyl ester and a methacrylic acid alkyl ester, and
(a3) a monomer selected from the group consisting of a polyoxyethylene alkyl ester of acrylic acid and a polyoxyethylene alkyl ester of methacrylic acid, and comprising 10 mol % or more of (a2) as represented by mol % based on the total monomers.
The copolymer as the component (A-1) is not limited as long as the copolymer comprises monomers selected from the group consisting of (a1), (a2), and (a3) as constitutional units and comprises 10 mol % or more of (a2) as represented by mol % based on the total monomers. The copolymer is not limited by its content ratio or binding pattern such as a block bond or a random bond. Also, the copolymer may contain other monomers and may have a cross-linked structure.
When the copolymer as the component (A-1) comprises a monomer other than the monomers selected from the group consisting of (a1), (a2), and (a3) as a constitutional unit, the content thereof is preferably less than 10 mol %, more preferably 5 mol % or less and further preferably 1 mol % or less, based on the total monomers.
In the acrylic acid alkyl ester and the methacrylic acid alkyl ester as (a2), the alkyl group of the alkyl ester preferably has 1 to 22 carbon atoms, more preferably 1 to 18 carbon atoms.
The mol % of (a2) in the copolymer (A-1) is 10 mol % or more, preferably 15 mol % or more, more preferably 20 mol % or more, from the viewpoint of obtaining a clean feeling of the skin after cleansing, and is preferably 70 mol % or less, more preferably 65 mol % or less and further preferably 60 mol % or less, from the viewpoint of obtaining stability, as represented by mol % based on the total monomers. The mol % of (a2) in the copolymer is preferably 10 to 70 mol %, more preferably 15 to 65 mol % and further preferably 20 to 60 mol % as represented by mol % based on the total monomers. The mol % refers to the molar percentage of the constitutional unit (a2) in the total moles of monomers as constitutional units in one polymer molecule.
Examples of the polymer (A-1) include a copolymer comprising a monomer selected from the group consisting of acrylic acid and methacrylic acid and a monomer selected from the group consisting of an acrylic acid alkyl ester and a methacrylic acid alkyl ester as constitutional units, polyquaternium-51, polyquaternium-61, and (glycerylamidoethyl methacrylate/stearyl methacrylate) copolymer, and the like.

A non-cross-linked anionic amphiphilic polymer comprising 50 to 90% by mass of at least one constitutional unit (hereinafter, also referred to as an anionic constitutional unit) selected from the group consisting of a constitutional unit represented by the following formula (3) and a constitutional unit represented by the following formula (4) in the total constitutional units, and 10 to 50% by mass of a constitutional unit (hereinafter, also referred to as a hydrophobic constitutional unit) consisting of a constitutional unit represented by the following formula (5) in the total constitutional units can be used as the copolymer comprising a monomer selected from the group consisting of acrylic acid and methacrylic acid and a monomer selected from the group consisting of an acrylic acid alkyl ester and a methacrylic acid alkyl ester as constitutional units:

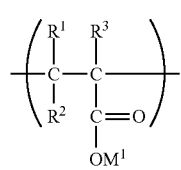

(3)

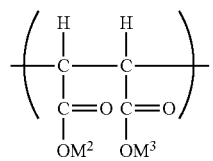

(4)

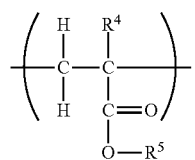

(5)

In formula (3), $R^1$, $R^2$ and $R^3$ each represent a hydrogen atom or a methyl group, and each of $R^1$ and $R^2$ is preferably a hydrogen atom. In the formulas (3) and (4), $M^1$, $M^2$, and $M^3$ each represent a hydrogen atom or a cationic group. Examples of the cationic group include: alkali metal ions such as sodium and potassium; and ammonium ions. Sodium or potassium is preferred. Also preferably, 5 mol % or more of carboxyl groups are in a salt form.

In formula (5), $R^4$ represents a hydrogen atom or a methyl group, and $R^5$ represents a linear or branched alkyl group or alkenyl group having 4 to 30 carbon atoms, preferably 8 to 30 carbon atoms, more preferably 12 to 22 carbon atoms, from the viewpoint of cleansing properties and emulsion stability. Specific examples thereof include an octyl group, a 2-ethylhexyl group, a decyl group, a lauryl group, a myristyl group, a cetyl group, a stearyl group, an oleyl group, and a behenyl group.

The ratio of the anionic constitutional unit in the total constitutional units of the anionic amphiphilic polymer as mentioned above is 50 to 90% by mass, preferably 50 to 85% by mass, more preferably 50 to 80% by mass, from the viewpoint of cleansing properties and emulsion stability. The ratio of the hydrophobic constitutional unit in the total constitutional units of the anionic amphiphilic polymer is 10 to 50% by mass, preferably 15 to 50% by mass, more preferably 20 to 50% by mass, from the viewpoint of cleansing properties and emulsion stability.

Such an anionic amphiphilic polymer can be manufactured by a method described in, for example, JP-A-2007-238549. A compound of Synthesis Example 1, 2, or 3 described in JP-A-2007-238549, or (acrylic acid/stearyl acrylate) copolymer can be used.

Further, a commercially available product can be used, for example, Lipidure PMB, Lipidure B, Lipidure NR, or Lipidure NA (manufactured by NOF Corp.) as polyquaternium-51; Lipidure S (manufactured by NOF Corp.) as polyquaternium-61; or Ceracute F, Ceracute L, or Ceracute V (manufactured by NOF Corp.) as (glycerylamidoethyl methacrylate/stearyl methacrylate) copolymer.

The component (A-1) is more preferably a copolymer comprising monomers (a1), (a2), and (a3) as constitutional units:

(a1) a monomer selected from the group consisting of acrylic acid and methacrylic acid, (a2) a monomer selected from the group consisting of an acrylic acid alkyl ester and a methacrylic acid alkyl ester, and (a3) a monomer selected from the group consisting of a polyoxyethylene alkyl ester of acrylic acid and a polyoxyethylene alkyl ester of methacrylic acid, and comprising 10 mol % or more of (a2) as represented by mol % based on the total monomers.

The copolymer is not limited as long as the copolymer comprises the monomers (a1), (a2), and (a3) as constitutional units. The copolymer is not limited by its content ratio or binding pattern such as a block bond or a random bond. Also, the copolymer may contain other monomers and may have a cross-linked structure.

In the acrylic acid alkyl ester and the methacrylic acid alkyl ester as (a2), the alkyl group of the alkyl ester preferably has 1 to 22 carbon atoms, more preferably 1 to 18 carbon atoms.

In the polyoxyethylene alkyl ester of acrylic acid and the polyoxyethylene alkyl ester of methacrylic acid as (a3), the addition molar number polyoxyethylene is preferably 10 to 30 and more preferably 12 to 25, and the alkyl group of the alkyl ester preferably has 12 to 22 carbon atoms and more preferably 18 to 22 carbon atoms. (a3) is more preferably an ester of acrylic acid and polyoxyethylene (20) stearyl ether, an ester of methacrylic acid and polyoxyethylene (20) stearyl ether, an ester of acrylic acid and polyoxyethylene (25) behenyl ether, or an ester of methacrylic acid and polyoxyethylene (25) behenyl ether.

The component (A-1) is preferably (acrylates/steareth-20 methacrylate) copolymer, (acrylates/steareth-20 methacrylate) crosspolymer, or (acrylates/beheneth-25 methacrylate) copolymer from the viewpoint of a high cleansing power and a clean feeling.

A commercially available product such as ACULYN 22, ACULYN 88, or ACULYN 28 (all manufactured by Rohm and Haas Company) can be used as the component (A-1). ACULYN 22 is a 30% by mass aqueous solution; CULYN 28 is a 20% by mass aqueous solution; and ACULYN 88 is a 29% by mass aqueous solution.

Examples of the copolymer comprising 10 mol % or more of (a2) as represented by mol % based on the total monomers as the component (A-1) include: Lipidure PMB and Lipidure B (manufactured by NOF Corp.) as polyquaternium-51; compounds of Synthesis Examples 1, 2, and 3 described in JP-A-2007-238549 and (acrylic acid/stearyl acrylate) copolymer; ACULYN 22, ACULYN 88, and ACULYN 28 (all manufactured by Rohm and Haas Company) as (acrylates/ steareth-20 methacrylate) copolymer, (acrylates/steareth-20 methacrylate) crosspolymer, and (acrylates/beheneth-25 methacrylate) copolymer. Examples of a copolymer comprising (a2) in an amount less than 10 mol % as represented by mol % based on the total monomers include acrylic acid/alkyl methacrylate copolymer, PEMULEN TR-1, PEMULEN TR-2, and Carbopol ETD2020 (all manufactured by Lubrizol Advanced Materials).

(A-2) A polysaccharide derivative having a polyoxyalkylene chain having an average molecular weight of 300 to 100,000 and having a constitutional unit represented by formula (1):

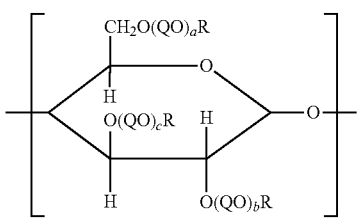

(1)

wherein R identically or differently represents a group selected from the group consisting of (d) a hydrogen atom, a methyl group, an ethyl group, a hydroxyethyl group, and a hydroxypropyl group, (e) a substituent comprising a polyoxyalkylene group, (f) a sulfoalkyl group, (g) a carboxyalkyl group, and (h) a cationic substituent; Q identically or differently represents an alkylene group having 2 to 4 carbon atoms; a, b, and c identically or differently represent a number of 0 to 10; the QO groups, the R groups, or the numbers a, b, and c are identical or different in each repeating unit or between repeating units; and when each of the substituents (e) to (h) has a hydroxy group, the hydroxy group is optionally further substituted by any of other substituents (e) to (h), provided that at least one or more substituents (e) exist as R.

(A-2) is preferably a polysaccharide derivative in which the hydrogen atoms of hydroxy groups in a polysaccharide or a derivative thereof are partially or completely replaced with (e) a substituent comprising a polyoxyalkylene group, wherein (e) is preferably a group represented by the following formula (6):

$$-E^1-(OA^1)_q-E^2-R^6 \quad (6)$$

wherein $E^1$ represents an optionally hydroxy group- or oxo group-substituted divalent saturated hydrocarbon group having 1 to 6 carbon atoms; q represents a number of 8 to 300; $A^1$, having a number of q units, identically or differently represent a divalent saturated hydrocarbon group having 1 to 6 carbon atoms; $E^2$ represents an ether bond or an oxycarbonyl group; and $R^6$ represents an optionally hydroxy group-substituted alkyl group having 4 to 30 carbon atoms.

The hydrocarbon group $E^1$ in formula (6) can be any optionally hydroxy group- or oxo group-substituted linear or branched hydrocarbon group having 1 to 6 carbon atoms and preferably has 2 or 3 carbon atoms. Specific examples thereof include an ethylene group, a propylene group, a trimethylene group, a 2-hydroxytrimethylene group, a 1-hydroxymethylethylene group, a 1-oxoethylene group, a 1-oxotrimethylene group, and a 1-methyl-2-oxoethylene group.

The divalent hydrocarbon group $A^1$ in formula (6) can be a linear or branched divalent hydrocarbon group having 1 to 6 carbon atoms and preferably has 2 or 3 carbon atoms. Specific examples thereof include an ethylene group, a propylene group, and a trimethylene group. q is an average number of the repeating unit —(OA$^1$)- and is preferably 8 to 100 and more preferably 10 to 60, from the viewpoint of a cleansing power and emulsion stability. A, having a number of q units, are identical or different. $E^2$ represents an ether bond (—O—) or an oxycarbonyl group (—OCO— or —COO—) and is preferably an ether bond.

The long-chain alkyl group $R^6$ in formula (6) is a linear or branched alkyl group having 4 to 30 carbon atoms, preferably 5 to 25 carbon atoms, more preferably 6 to 20 carbon atoms. Specific examples thereof include an octyl group, a decyl group, a dodecyl group, a tetradecyl group, a hexadecyl group, an octadecyl group, and an isostearyl group. Among them, a linear alkyl group is preferred from the viewpoint of a cleansing power and emulsion stability.

The substitution degree of the group represented by formula (6) in the polysaccharide derivative is preferably 0.0001 to 1.0, more preferably 0.0005 to 0.5 and further preferably 0.001 to 0.1, per constituent monosaccharide residue.

The polysaccharide derivative (A-2) may be further substituted by one or more groups selected from the group consisting of substituents (f), (g), and (h) given below, in addition to the substituent (e). Also, a hydrogen atom of a hydroxy group in the substituents (e) to (h) may be further replaced by any one of substituents (e) to (h).

(f) An optionally hydroxy group-substituted sulfoalkyl group having 1 to 5 carbon atoms or a salt thereof:

Examples of the substituent (f) include a 2-sulfoethyl group, a 3-sulfopropyl group, a 3-sulfo-2-hydroxypropyl group, a 2-sulfo-1-(hydroxymethyl)ethyl group, and the like. Among them, a 3-sulfo-2-hydroxypropyl group is preferred from the viewpoint of stability and production. The whole or a portion of the substituent (f) may be in the form of a salt with a group 1 or 2 element (e.g., Na, K, Ca, Mg), amine, or an organic cation (e.g., ammonium), or the like. The substitution degree by the substituent (f) is preferably in the range of 0 to 1.0, more preferably 0 to 0.8 and further preferably 0 to 0.5, per constituent monosaccharide residue.

(g) An optionally hydroxy group-substituted carboxyalkyl group having 2 to 6 carbon atoms or a salt thereof:

Examples of the substituent (g) include a carboxymethyl group, a carboxyethyl group, a carboxypropyl group, a carboxybutyl group, a carboxypentyl group, and the like. Among them, a carboxymethyl group is preferred from the viewpoint of stability and production. The whole or a portion of the substituent (g) may be in the form of a salt with a group 1 or 2 element (e.g., Na, K, Ca, Mg), amine, or an organic cation (e.g., ammonium), or the like. The substitution degree by the substituent (g) is preferably in the range of 0 to 1.0, more preferably 0 to 0.8 and further preferably 0 to 0.5, per constituent monosaccharide residue.

(h) A group represented by the following formula (7):

(7)

wherein $D^1$ represents an optionally hydroxy group-substituted linear or branched divalent saturated hydrocarbon group having 1 to 6 carbon atoms; $R^7$, $R^8$, and $R^9$ identically or differently represent an optionally hydroxy group-substituted linear or branched alkyl group having 1 to 3 carbon atoms; and $X^-$ represents a hydroxy ion, a halogen ion, or an organic acid ion.

$D^1$ in the cationic substituent (h) preferably has 2 or 3 carbon atoms. Specifically, ethylene, propylene, trimethylene, 2-hydroxytrimethylene, 1-hydroxymethylethylene, or the like is preferred.

Examples of $R^7$, $R^8$, and $R^9$ in the cationic substituent (h) include a methyl group, an ethyl group, a propyl group, and a 2-hydroxyethyl group, and the like.

Among them, a methyl group or an ethyl group is preferred.

Examples of the halogen ion represented by $X^-$ in the cationic substituent (h) include a chlorine ion, a bromine ion, and an iodine ion, and the like. Examples of the organic acid ion include $CH_3COO^-$, $CH_3CH_2COO^-$, $CH_3(CH_2)_2COO^-$, and the like. $X^-$ is preferably a hydroxy ion, a chlorine ion, or a bromine ion.

The degree of substitution by the cationic substituent (h) is in the range of preferably 0 to 0.5, more preferably 0 to 0.3, per constituent monosaccharide residue.

Polysaccharide derivatives as described in, for example, International Publication No. WO 00/73351 pamphlet or JP-A-2005-336116 can be used. Examples thereof include hydroxyethyl(hydroxypropylpolyethylene glycol dodecyl ether)cellulose and (laureth-13 PG-hydroxyethylcellulose), and the like.

(A-2) is preferably hydroxyethyl(hydroxypropylpolyethylene glycol dodecyl ether)cellulose or (laureth-13 PG-hydroxyethylcellulose) from the viewpoint of obtaining a cleansing sensation.

(A-3) A polyether polycarbonate having a constitutional unit represented by formula (2):

wherein $A^2$ represents an alkylene group having 2 to 6 carbon atoms; n represents a number of 5 to 1,000 on average; p represents a number of 5 to 100 on average; $A^2$, having a number of (n×p) units, may be identical or different.

In formula (2), $A^2$ represents an alkylene group having 2 to 6 carbon atoms, and A2, having a number of (n×p) units, may be identical or different and preferably at least two or more alkylene groups. $A^2$ is preferably an alkylene group having 2 to 4 carbon atoms, more preferably an alkylene group having 2 or 3 carbon atoms and further preferably a mixed group of an ethylene group and a propylene group. In case $A^2$ consists of different alkyleneoxy groups, these groups may have a block structure or a random structure and more preferably have a random structure.

In formula (2), n is a number of 5 to 1,000 indicating the average addition molar number of the alkyleneoxy groups and is preferably a number of 10 to 500. p is a number of 5 to 100 indicating the average repetition number of the $[(A^2O)_nCOO]$ group and is preferably a number of 5 to 50.

The weight-average molecular weight of the polyether polycarbonate is preferably 50,000 or larger, more preferably 100,000 or larger, further preferably 150,000 or larger and particularly preferably 200,000 or larger, from the viewpoint of cleansing properties. The weight-average molecular weight of the polyether polycarbonate is preferably 1,000,000 or smaller, more preferably 700,000 or smaller and further preferably 500,000 or smaller, from the viewpoint of cleansing properties.

The polyether polycarbonate as the component (A-3) can be manufactured by a method described in, for example, JP-A-2009-41004, and a compound of Synthesis Example 1, 2, or 3 described in JP-A-2009-41004 can be used.

(A-3) is preferably a compound of Synthesis Example 1, 2, or 3 described in JP-A-2009-41004 from the viewpoint of obtaining a clean feeling.

The component (A) is preferably (A-1), more preferably (A-1) which is a copolymer comprising (a1), (a2), and (a3) as constitutional units and comprising 10 mol % or more of (a2) based on the total monomers, and further preferably (acrylates/steareth-20 methacrylate) copolymer, (acrylates/steareth-20 methacrylate) crosspolymer, or (acrylates/beheneth-25 methacrylate) copolymer, from the viewpoint of obtaining a cleansing power and obtaining a clean feeling by refreshing the skin after cleansing.

One or two or more in combination of the components (A) can be used. The content thereof in the total composition is preferably 0.001% by mass or more, more preferably 0.005% by mass or more, further preferably 0.01% by mass or more and even further preferably 0.03% by mass or more, from the viewpoint of reducing oil agents remaining on the skin after cleansing, and is preferably 5% by mass or less, more preferably 3% by mass or less and further preferably 2% by mass or less, from the viewpoint of suppressing stickiness. The content of the component (A) in the total composition is preferably 0.001 to 5% by mass, more preferably 0.005 to 3% by mass, further preferably 0.01 to 2% by mass and even further preferably 0.03 to 2% by mass.

Examples of the ether oil (b1) as the component (B) include cetyl-1,3-dimethylbutyl ether, dicaprylyl ether, dicapryl ether, dilauryl ether, and diisostearyl ether. Among them, cetyl-1,3-dimethylbutyl ether and dicaprylyl ether are preferred from the viewpoint of obtaining a high cleansing power and a fresh feeling.

One or two or more in combination of the components (b1) can be used. The content thereof in the total composition is preferably 1% by mass or more, more preferably 3% by mass or more and further preferably 5% by mass or more, from the viewpoint of a cleansing power, and is preferably 50% by mass or less, more preferably 30% by mass or less and further preferably 15% by mass or less, from the viewpoint of a fresh feeling. The content of the component (b1) in the total composition is preferably 1 to 50% by mass, more preferably 3 to 30% by mass and further preferably 5 to 15% by mass.

In the present invention, the mass ratio of the component (b1) to the component (A), (b1)/(A) is preferably 0.5 or more, more preferably 1 or more, further preferably 2 or more and even further preferably 3 or more, from the viewpoint of a cleansing power, and is preferably 400 or less, more preferably 300 or less and further preferably 200 or less, from the viewpoint of obtaining a cleansing feeling. The mass ratio of the component (b1) to the component (A), (b1)/(A) is preferably 0.5 to 400, more preferably 1 to 300, further preferably 2 to 200 and even further preferably 3 to 200.

The hydrocarbon oil (b2) as the component (B) has a viscosity of 18 mPa·s or lower, preferably 10 mPa·s or lower, at 30° C. In this context, the viscosity was measured using a BM-type viscometer (manufactured by Tokimec, Inc., measurement conditions: rotor No. 1, 60 rpm).

Examples of the component (b2) include liquid isoparaffins such as light liquid isoparaffin and hydrogenated polyisobutene, isododecane, and isohexadecane. Among them, light liquid isoparaffin, isododecane, or isohexadecane is preferred from the viewpoint of obtaining a high cleansing power and a fresh feeling.

One or two or more in combination of the components (b2) can be used. The content thereof in the total composition is preferably 1% by mass or more, more preferably 3% by mass or more and further preferably 4% by mass or more, from the viewpoint of a cleansing power, and is preferably 50% by mass or less, more preferably 40% by mass or less and further preferably 30% by mass or less, from the viewpoint of a fresh feeling. The content of the component (b2) in the total composition is preferably 1 to 50% by mass, more preferably 3 to 40% by mass and further preferably 4 to 30% by mass.

In the present invention, the mass ratio of the component (b2) to the component (A), (b2)/(A) is preferably 0.5 or more, more preferably 1 or more and further preferably 2 or more, from the viewpoint of a cleansing power, and is preferably 400 or less, more preferably 300 or less and further preferably 200 or less, from the viewpoint of obtaining a clean feeling. The mass ratio of the component (b2) to the component (A), (b2)/(A) is preferably 0.5 to 400, more preferably 1 to 300 and further preferably 2 to 200.

In the component (B), the content of (b2) is preferably an amount exceeding 35% by mass, more preferably 40% by mass or more, in the total oil agents except for (b1) from the viewpoint of obtaining a cleansing power and reducing the oil amount remaining on the skin.

When the components (b1) and (b2) are used in combination, the mass ratio of the components (b1) to (b2), (b1)/(b2) is preferably 0.05 or more, more preferably 0.1 or more and further preferably 0.3 or more, for reducing a frictional feeling on the skin after wiping, and is preferably 30 or less, more preferably 10 or less, further preferably 3.5 or less, for reducing stickiness of the skin after wiping. The mass ratio of the components (b1) to (b2), (b1)/(b2) is preferably 0.05 to 30, more preferably 0.1 to 10 and further preferably 0.3 to 3.5.

One selected from the group consisting of the components (b1) and (b2) or two or more in combination can be used as the components (B). The component (B) preferably comprises the component (b1) and more preferably comprises both components (b1) and (b2) at the same time.

The total content of (b1) and (b2) used in combination in the total composition is preferably 1% by mass or more, more preferably 3% by mass or more, further preferably 4% by mass or more and even further preferably 9% by mass or more, and is preferably 50% by mass or less, more preferably 40% by mass or less, further preferably 30% by mass or less. The total content of the components (B) in the total composition is preferably 1 to 50% by mass, more preferably 3 to 40% by mass, further preferably 4 to 30% by mass and even further preferably 9 to 30% by mass.

In the present invention, the mass ratio of the component (B) to the component (A), (B)/(A) is preferably 0.5 or more, more preferably 1 or more and further preferably 2 or more, from the viewpoint of a cleansing power, and is preferably 400 or less, more preferably 300 or less, further preferably 200 or less, from the viewpoint of obtaining a clean feeling. The mass ratio of the component (B) to the component (A), (B)/(A) is preferably 0.5 to 400, more preferably 1 to 300 and further preferably 2 to 200.

In the present invention, water as the component (C) balances the components. The content thereof in the total composition is preferably 20% by mass or more, more preferably 30% by mass or more and further preferably 40% by mass or more. It is also preferably 95% by mass or less, more preferably 90% by mass or less and further preferably 85% by mass or less.

The component (D) used in the present invention is a nonionic surfactant having HLB of 8 or more and preferably HLB of 8 to 15, thereby it produces higher stability and higher cleansing performance.

In this context, HLB refers to an index which indicates a hydrophilic-lipophilic balance. In the present invention, a value calculated using the following expression of Oda, Teramura, et al. is used:

$$HLB = \frac{\sum \text{Inorganic value}}{\sum \text{Organic value}} \times 10$$

Examples of the component (D) include polyglycerin fatty acid ester, polyethylene glycol fatty acid ester, polyoxyethylene glycerin fatty acid ester, polyoxyethylene polyoxypropylene glycol, polyoxyethylene sorbitan fatty acid ester, polyoxyethylene sorbit fatty acid ester, polyoxyethylene castor oil, polyoxyethylene hydrogenated castor oil, polyoxyethylene hydrogenated castor oil fatty acid ester, polyoxyethylene alkyl ether, polyoxyethylene alkyl ether fatty acid ester, sucrose fatty acid ester, alkyl polyglucoside, and (poly)alkyl glyceryl ether, etc. Among them, preferred are polyglycerin fatty acid ester, polyethylene glycol fatty acid ester, polyoxyethylene glycerin fatty acid ester, polyoxyethylene sorbitan fatty acid ester, and polyoxyethylene hydrogenated castor oil fatty acid ester, from the viewpoint of improving stability.

The composition comprises no component (D), or one component (D), or two or more thereof in combination, if any. The content thereof in the total composition is preferably 0.005% by mass or more, more preferably 0.05% by mass or more and further preferably 0.1% by mass or more, and is less than 5% by mass, preferably 2% by mass or less and more preferably 1% by mass or less, from the viewpoint of stability. The content of the component (D) in the total composition is preferably 0.005% by mass or more and less than 5% by mass, more preferably 0.05 to 2% by mass and further preferably 0.1 to 1% by mass.

Combined use of the component (D) with a nonionic surfactant having HLB less than 8 is more preferred from the viewpoint of stability. Examples of the nonionic surfactant having HLB less than 8 include: polyethylene glycol-based surfactants such as ethylene glycol fatty acid ester (e.g., ethylene glycol monostearic acid ester), polyethylene glycol fatty acid ester (e.g., polyethylene glycol (2) monostearic acid ester), polyethylene glycol alkyl ether (e.g., polyethylene glycol (5) decyl pentadecyl ether), and polyethylene glycol hydrogenated castor oil (e.g., polyethylene glycol (5) hydrogenated castor oil monoisolaurate); propylene glycol-based surfactants such as propylene glycol fatty acid ester, polypropylene glycol fatty acid ester, propylene glycol alkyl ether, polypropylene glycol alkyl ether, and oxidized ethylene derivatives of propylene glycol alkyl ether; glycerin fatty acid ester such as glycerin monoisostearic acid ester; glycerin alkyl ether such as glycerin monoisostearyl ether; and sorbitan fatty acid ester such as sorbitan monostearic acid ester, and the like. Among them, glycerin fatty acid ester, sorbitan fatty acid ester, and glycerin alkyl ether are preferred.

One or two or more in combination of the nonionic surfactants having HLB less than 8 can be used. The content thereof in the total composition is preferably zero or less than 5% by mass from the viewpoint of stability. The content of the nonionic surfactant having HLB less than 8 in the total composition is preferably 0.005% by mass or more, more preferably 0.05% by mass or more, further preferably 0.1% by mass or more, and is preferably less than 5% by mass, more preferably 2% by mass or less, further preferably 1% by mass or less. The content of the nonionic surfactant having HLB less than 8 in the total composition is preferably 0.005% by mass or more and less than 5% by mass, more preferably 0.05 to 2% by mass, further preferably 0.1 to 1% by mass.

The cleansing composition of the present invention can further comprise (E) a polyol. Examples of the polyol include polyhydric alcohols, polyglycerin, polyethylene glycol, polypropylene glycol, and sugars.

More specifically, examples of the polyhydric alcohols include ethylene glycol, propylene glycol, isoprene glycol, 1,3-butylene glycol, hexylene glycol, trimethylolpropane, and glycerin. Among them, propylene glycol, isoprene glycol, 1,3-butylene glycol, hexylene glycol, and glycerin are preferred, and 1,3-butylene glycol, propylene glycol, isoprene glycol, and glycerin are more preferred from the viewpoint of a moist feeling of the skin after wiping.

Examples of the polyglycerin, the polyethylene glycol, and the polypropylene glycol include polyglycerin having a molecular weight of 2,000 or smaller, polyethylene glycol having a molecular weight of 10,000 or smaller, and polypropylene glycol having a molecular weight of 1,000 or smaller. Among them, diglycerin, polyethylene glycol 200, polyethylene glycol 400, polyethylene glycol 1000, polyethylene glycol 1540, dipropylene glycol, polypropylene glycol (3), and polypropylene glycol (7) are preferred from the viewpoint of a moist feeling of the skin after wiping.

Examples of the sugars include sorbitol, erythritol, pentaerythritol, methyl glucoside, ethyl glucoside, polyoxyethylene methyl glucoside, and polyoxypropylene methyl glucoside. Alkyl glucoside with an alkyl chain having 2 or less carbon atoms is preferred. Among them, methyl glucoside, ethyl glucoside, polyoxyethylene methyl glucoside, and polyoxypropylene methyl glucoside are preferred, and polyoxyethylene methyl glucoside and polyoxypropylene methyl glucoside are more preferred from the viewpoint of a moist feeling of the skin after wiping.

One or two or more in combination of the polyols can be used as the components (E). The content thereof in the total composition is preferably 0.1 to 30% by mass, more preferably 0.5 to 20% by mass, further preferably 1 to 15% by mass, from the viewpoint of the balance between a moist feeling and reduction in stickiness.

The cleansing composition of the present invention can further comprise (F) ethanol which can thereby further enhance a clean feeling. The content of the ethanol (F) in the total composition is preferably 0.1 to 30% by mass, more preferably 0.5 to 20% by mass and further preferably 1 to 15% by mass.

The cleansing composition of the present invention can contain, in addition to the components mentioned above, those components used in usual cleansing compositions to the extent not inhibiting the effects of the present invention. The cleansing composition of the present invention can contain, for example, an oil agent other than the component (B), a thickener other than the component (A), an anionic surfactant, a cationic surfactant, an amphoteric surfactant, a bactericide, an anti-inflammatory agent, an antiseptic, a chelating agent, a salt, a pearling agent, a fragrance, a cooling agent, a dye, an antioxidant, and a plant extract.

Examples of the oil agent other than the component (B) include hydrocarbon oils, such as liquid paraffin, having a viscosity exceeding 18 mPa·s at 30° C. One or two or more in combination of the oil agents other than the component (B) can be used. The content thereof in the total composition is preferably 0.01% by mass or more, and is preferably 50% by mass or less, more preferably 40% by mass or less, further preferably 30% by mass or less and even further preferably 20% by mass or less.

The composition is preferably free from the anionic surfactant, the cationic surfactant, and the amphoteric surfactant, except that these surfactants are irreversibly mixed thereinto to the extent not inhibiting the effects of the present invention.

The cleansing composition of the present invention can be prepared by uniformly mixing an aqueous phase containing the copolymer as the component (A) and water, neutralizing the aqueous phase by the addition of an alkali agent such as sodium hydroxide or potassium hydroxide, and then adding other components thereto. The composition comprising a starting material which is solid at normal temperature can be prepared by thermally melting the solid material or dissolving the solid material in other components and then uniformly mixing all components.

The cleansing composition of the present invention is suitable, for example, as a skin cleansing composition such as a facial wash or a cleansing agent, more preferably a cleansing agent. The composition is preferably used for cleansing a makeup cosmetic applied on the face.

The cleansing composition of the present invention can be used by, for example, a method of applying the composition on a cotton etc. and wiping the skin with the cotton etc., where the composition may be used as it is or after shaking it up till uniform if it is a separated composition; a method of wiping with a cotton etc. after applying the composition to the skin with a hand; a method of washing off after applying the composition to the skin with a hand; a method of washing after dipping the composition to a cotton etc. and applying the composition on the skin; a method of washing off after wiping the skin according to any one of the above methods. The composition can be also used in a form in which a sheet is impregnated with the composition. The composition can be used, preferably by a method of applying the composition on a cotton etc. and wiping the skin with the cotton etc., more preferably by a method of wiping with a cotton etc. after applying the composition to the skin with a hand.

The skin cleansing composition according to the second aspect of the present invention can produce a high cleansing power for even a stay-put makeup such as waterproof mascara, offer a clean feeling without oil agents remaining on the skin after cleansing, and offer a moist bare skin feeling.

The polymer as the component (G) used in the second aspect of the present invention is selected from the group consisting of (G-1), (G-2), and (G-3).

(G-1) A copolymer comprising monomers selected from the group consisting of (g1), (g2), and (g3) as constitutional units:

(g1) a monomer selected from the group consisting of acrylic acid and methacrylic acid, (g2) a monomer selected from the group consisting of an acrylic acid alkyl ester and a methacrylic acid alkyl ester, and (g3) a monomer selected from the group consisting of a polyoxyethylene alkyl ester of acrylic acid and a polyoxyethylene alkyl ester of methacrylic acid, and comprising 10 mol % or more of the monomer unit (g2) based on the total monomers.

The copolymer as the component (G-1) is not limited as long as the copolymer comprises monomers selected from the group consisting of (g1), (g2), and (g3) as constitutional units and comprises 10 mol % or more of (g2) as represented by mol % based on the total monomers. The copolymer is not limited by its content ratio or binding pattern such as a block bond or a random bond. Also, the copolymer may contain other monomers and may have a cross-linked structure.

When the copolymer as the component (G-1) comprises a monomer other than the monomers selected from the group consisting of (g1), (g2), and (g3) as a constitutional unit, the content thereof is preferably less than 10 mol %, more preferably 5 mol % or less, further preferably 1 mol % or less based on the total monomers.

In the acrylic acid alkyl ester and the methacrylic acid alkyl ester as (g2), the alkyl group of the alkyl ester preferably has 1 to 22 carbon atoms, more preferably 1 to 18 carbon atoms.

The content of the monomer unit (g2) in the copolymer (G-1) based on the total monomers in the molecule is 10 mol % or more, preferably 15 mol % or more, more preferably 20 mol % or more, from the viewpoint of obtaining a clean feeling of the skin after cleansing, and is preferably 70 mol % or less, more preferably 65 mol % or less, further preferably 60 mol % or less, from the viewpoint of obtaining stability. The content of the monomer unit (g2) in the copolymer based on the total monomers in the molecule is preferably 10 to 70 mol %, more preferably 15 to 65 mol % and further preferably 20 to 60 mol %.

(g2) is a hydrophobic constitutional unit in the polymer as the component (G). The polymer (G), albeit water-soluble, comprises 10 mol % or more of the hydrophobic monomer. Such a hydrophobic constitutional unit contained at 10 mol % or more is considered to enhance oil dispersibility and to prevent oil from remaining on the skin after cleansing, in spite of high cleansing properties.

Examples of the polymer (G-1) include a copolymer comprising a monomer selected from the group consisting of acrylic acid and methacrylic acid and a monomer selected from the group consisting of an acrylic acid alkyl ester and a methacrylic acid alkyl ester as constitutional units, polyquaternium-51, polyquaternium-61, and (glycerylamidoethyl methacrylate/stearyl methacrylate) copolymer.

A non-cross-linked anionic amphiphilic polymer comprising 50 to 90% by mass of at least one constitutional unit (hereinafter, also referred to as an anionic constitutional unit) selected from the group consisting of a constitutional unit represented by the following formula (3) and a constitutional unit represented by the following formula (4) in the total constitutional units, and 10 to 50% by mass of a constitutional unit (hereinafter, also referred to as a hydrophobic constitutional unit) represented by the following formula (5) in the total constitutional units can be used as the copolymer comprising a monomer selected from the group consisting of acrylic acid and methacrylic acid and a monomer selected from the group consisting of an acrylic acid alkyl ester and a methacrylic acid alkyl ester as constitutional units:

(3)

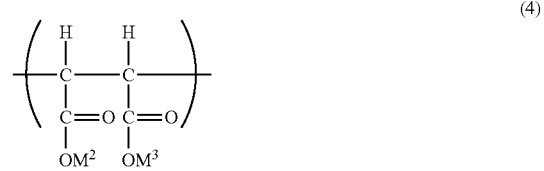

(4)

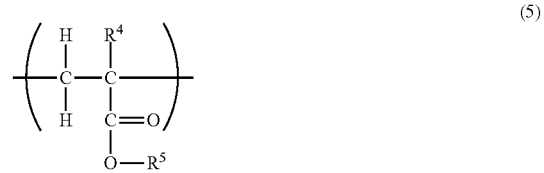

(5)

In formula (3), $R^1$, $R^2$, and $R^3$ each represent a hydrogen atom or a methyl group, and each of $R^1$ and $R^2$ is preferably a hydrogen atom. In formulas (3) and (4), $M^1$, $M^2$, and $M^3$ each represent a hydrogen atom or a cationic group. Examples of the cationic group include: alkali metal ions such as sodium and potassium; and ammonium ions. Sodium or potassium is preferred. Also preferably, 5 mol % or more of carboxyl groups are in a salt form.

In formula (5), $R^4$ represents a hydrogen atom or a methyl group, and $R^5$ represents a linear or branched alkyl group or alkenyl group having 4 to 30 carbon atoms, preferably 8 to 30 carbon atoms, more preferably 12 to 22 carbon atoms, from the viewpoint of cleansing properties and emulsion stability. Specific examples thereof include an octyl group, a 2-ethylhexyl group, a decyl group, a lauryl group, a myristyl group, a cetyl group, a stearyl group, an oleyl group, and a behenyl group.

The ratio of the anionic constitutional unit in the total constitutional units of the anionic amphiphilic polymer as mentioned above is 50 to 90% by mass, preferably 50 to 85% by mass and more preferably 50 to 80% by mass, from the viewpoint of cleansing properties and emulsion stability. The ratio of the hydrophobic constitutional unit in the total constitutional units of the anionic amphiphilic polymer is 10 to 50% by mass, preferably 15 to 50% by mass and more preferably 20 to 50% by mass, from the viewpoint of cleansing properties and emulsion stability.

Such an anionic amphiphilic polymer can be manufactured by a method described in, for example, JP-A-2007-238549, and a compound of Synthesis Example 1, 2, or 3 described in JP-A-2007-238549, or (acrylic acid/stearyl acrylate) copolymer can be used.

Alternatively, a commercially available product can be used, for example, Lipidure PMB, Lipidure B, Lipidure NR, or Lipidure NA (manufactured by NOF Corp.) as polyquaternium-51; Lipidure S (manufactured by NOF Corp.) as polyquaternium-61; or Ceracute F, Cute L, or Cute V (manufactured by NOF Corp.) as (glycerylamidoethyl methacrylate/stearyl methacrylate) copolymer.

The component (G-1) is more preferably a copolymer comprising monomers (g1), (g2), and (g3) as constitutional units:
(g1) a monomer selected from the group consisting of acrylic acid and methacrylic acid,
(g2) a monomer selected from the group consisting of an acrylic acid alkyl ester and a methacrylic acid alkyl ester, and
(g3) a monomer selected from the group consisting of a polyoxyethylene alkyl ester of acrylic acid and a polyoxyethylene alkyl ester of methacrylic acid, and comprising 10 mol % or more of the monomer unit (g2) based on the total monomers.

The copolymer is not limited as long as the copolymer comprises the monomers (g1), (g2), and (g3) as constitutional units. The copolymer is not limited by its content ratio or binding pattern such as a block bond or a random bond. Also, the copolymer may contain other monomers and may have a cross-linked structure.

In the acrylic acid alkyl ester and the methacrylic acid alkyl ester as (g2), the alkyl group of the alkyl ester preferably has 1 to 22 carbon atoms and more preferably 1 to 18 carbon atoms.

In the polyoxyethylene alkyl ester of acrylic acid and the polyoxyethylene alkyl ester of methacrylic acid as (g3), the addition molar number of polyoxyethylene is preferably 10 to 30 and more preferably 12 to 25, and the alkyl group of the alkyl ester preferably has 12 to 22 carbon atoms and more preferably 18 to 22 carbon atoms. (g3) is more preferably ester of acrylic acid and polyoxyethylene (20) stearyl ether, ester of methacrylic acid and polyoxyethylene (20) stearyl ether, ester of acrylic acid and polyoxyethylene (25) behenyl ether, or ester of methacrylic acid and polyoxyethylene (25) behenyl ether.

The component (G-1) is preferably acrylates/steareth-20 methacrylate) copolymer, (acrylates/steareth-20 methacrylate) crosspolymer, or (acrylates/beheneth-25 methacrylate) copolymer comprising 20 mol % or more of the monomer unit (g2) based on the total monomers from the viewpoint of a high cleansing power and a clean feeling.

A commercially available product such as ACULYN 22, ACULYN 88, or ACULYN 28 (all manufactured by Rohm and Haas Company) can be used as the component (G-1). ACULYN 22 is a 30% by mass aqueous solution; ACULYN 28 is a 20% by mass aqueous solution; and ACULYN 88 is a 29% by mass aqueous solution.

Examples of the copolymer comprising 10 mol % or more of the monomer unit (g2) based on the total monomers as the component (G-1) include: Lipidure PMB and Lipidure B (manufactured by NOF Corp.) as polyquaternium-51; compounds of Synthesis Examples 1, 2, and 3 described in JP-A-2007-238549 and (acrylic acid/stearyl acrylate) copolymer; and ACULYN 22, ACULYN 88, and ACULYN 28 (all manufactured by Rohm and Haas Company) as (acrylates/steareth-20 methacrylate) copolymer, (acrylates/steareth-20 methacrylate) crosspolymer, and (acrylates/beheneth-25 methacrylate) copolymer. Examples of a copolymer comprising (a2) in an amount less than 10 mol % as represented by mol % based on the total monomers include acrylic acid/alkyl methacrylate copolymer, PEMULEN TR-1, PEMULEN TR-2, and Carbopol ETD2020 (all manufactured by Lubrizol Advanced Materials).

(G-2) A polysaccharide derivative having a polyoxyalkylene chain having an average molecular weight of 300 to 100,000 and having a constitutional unit represented by formula (1):

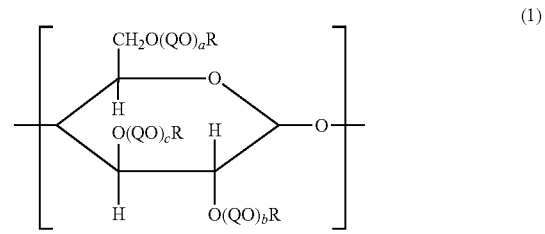

wherein R identically or differently represents a group selected from the group consisting of (d) a hydrogen atom, a methyl group, an ethyl group, a hydroxyethyl group, and a hydroxypropyl group, (e) a substituent comprising a polyoxyalkylene group, (f) a sulfoalkyl group, (g) a carboxyalkyl group, and (h) a cationic substituent; Q identically or differently represents an alkylene group having 2 to 4 carbon atoms; a, b, and c identically or differently represent a number of 0 to 10; the QO groups, the R groups, or the numbers a, b, and c are identical or different in each repeating unit or between repeating units; and when each of the substituents (e) to (h) has a hydroxy group, the hydroxy group is optionally further substituted by any of other substituents (e) to (h), provided that at least one or more substituents (e) exist as R.

(G-2) is preferably a polysaccharide derivative in which the hydrogen atoms of hydroxy groups in a polysaccharide or a derivative thereof are partially or completely replaced with (e) a substituent comprising a polyoxyalkylene group, wherein (e) is preferably a group represented by the following formula (6):

$$-E^1-(OA^1)_q-E^2-R^6 \qquad (6)$$

wherein $E^1$ represents an optionally hydroxy group- or oxo group-substituted divalent saturated hydrocarbon group having 1 to 6 carbon atoms; q represents a number of 8 to 300; $A^1$, having a number of q units, identically or differently represent a divalent saturated hydrocarbon group having 1 to 6 carbon atoms; $E^2$ represents an ether bond or an oxycarbonyl group; and $R^6$ represents an optionally hydroxy group-substituted alkyl group having 4 to 30 carbon atoms.

The hydrocarbon group $E^1$ in the formula (6) can be any optionally hydroxy group- or oxo group-substituted linear or branched hydrocarbon group having 1 to 6 carbon atoms and preferably has 2 or 3 carbon atoms. Specific examples thereof include an ethylene group, a propylene group, a trimethylene group, a 2-hydroxytrimethylene group, a 1-hydroxymethylethylene group, a 1-oxoethylene group, a 1-oxotrimethylene group, and a 1-methyl-2-oxoethylene group.

The divalent hydrocarbon group $A^1$ in formula (6) can be any linear or branched divalent hydrocarbon group having 1 to 6 carbon atoms and preferably has 2 or 3 carbon atoms. Specific examples thereof include an ethylene group, a propylene group, and a trimethylene group. q is the average number of the repeating unit —(OA¹)- and is preferably 8 to 100 and more preferably 10 to 60, from the viewpoint of a cleansing power and emulsion stability. A, having a number of q units, are identical or different. $E^2$ represents an ether bond (—O— or an oxycarbonyl group (—OCO— or —COO—) and is preferably an ether bond.

The long-chain alkyl group $R^6$ in formula (6) is a linear or branched alkyl group having 4 to 30 carbon atoms, preferably 5 to 25 carbon atoms and more preferably 6 to 20 carbon atoms. Specific examples thereof include an octyl group, a decyl group, a dodecyl group, a tetradecyl group, a hexadecyl group, an octadecyl group, and an isostearyl group. Among them, a linear alkyl group is preferred from the viewpoint of a cleansing power and emulsion stability.

The degree of substitution of the group represented by formula (6) in the polysaccharide derivative is preferably 0.0001 to 1.0, more preferably 0.0005 to 0.5 and further preferably 0.001 to 0.1, per constituent monosaccharide residue.

The polysaccharide derivative (G-2) may be further substituted by one or more groups selected from the group consisting of substituents (f), (g), and (h) given below, in addition to the substituent (e). Also, the hydrogen atom of a hydroxy group in the substituents (e) to (h) may be further replaced with any of substituents (e) to (h).

(f) An optionally hydroxy group-substituted sulfoalkyl group having 1 to 5 carbon atoms or a salt thereof:

Examples of the substituent (f) include a 2-sulfoethyl group, a 3-sulfopropyl group, a 3-sulfo-2-hydroxypropyl group, and a 2-sulfo-1-(hydroxymethyl)ethyl group. Among them, a 3-sulfo-2-hydroxypropyl group is preferred from the viewpoint of stability and production. The whole or a portion of the substituent (f) may be in the form of a salt with a group 1 or 2 element such as Na, K, Ca, or Mg, an organic cation such as an amine or ammonium, or the like. The degree of substitution by the substituent (f) is in the range of preferably 0 to 1.0, more preferably 0 to 0.8 and further preferably 0 to 0.5, per constituent monosaccharide residue.

(g) An optionally hydroxy group-substituted carboxyalkyl group having 2 to 6 carbon atoms or a salt thereof:

Examples of the substituent (g) include a carboxymethyl group, a carboxyethyl group, a carboxypropyl group, a carboxybutyl group, and a carboxypentyl group. Among them, a carboxymethyl group is preferred from the viewpoint of stability and production. The whole or a portion of the substituent (g) may be in the form of a salt with a group 1 or 2 element such as Na, K, Ca, or Mg, an organic cation such as an amine or ammonium, or the like. The degree of substitution by the substituent (g) is in the range of preferably 0 to 1.0, more preferably 0 to 0.8 and further preferably 0 to 0.5, per constituent monosaccharide residue.

(h) A group represented by the following formula (7):

wherein $D^1$ represents an optionally hydroxy group-substituted linear or branched divalent saturated hydrocarbon group having 1 to 6 carbon atoms; $R^7$, $R^8$, and $R^9$ identically or differently represent an optionally hydroxy group-substituted linear or branched alkyl group having 1 to 3 carbon atoms; and $X^-$ represents a hydroxy ion, a halogen ion, or an organic acid ion.

$D^1$ in the cationic substituent (h) preferably has 2 or 3 carbon atoms. Specifically, ethylene, propylene, trimethylene, 2-hydroxytrimethylene, 1-hydroxymethylethylene, or the like is preferred.

Examples of $R^7$, $R^8$, and $R^9$ in the cationic substituent (h) include a methyl group, an ethyl group, a propyl group, and a 2-hydroxyethyl group. Among them, a methyl group or an ethyl group is preferred.

Examples of the halogen ion represented by $X^-$ in the cationic substituent (h) include a chlorine ion, a bromine ion, and an iodine ion. Examples of the organic acid ion include $CH_3COO^-$, $CH_3CH_2COO^-$, and $CH_3(CH_2)_2COO^-$. $X^-$ is preferably a hydroxy ion, a chlorine ion, or a bromine ion.

The degree of substitution by the cationic substituent (h) is in the range of preferably 0 to 0.5 and more preferably 0 to 0.3, per constituent monosaccharide residue.

A polysaccharide derivative described in, for example, International Publication No. WO 00/73351 or JP-A-2005-336116 can be used as such a polysaccharide derivative. Examples thereof include hydroxyethyl(hydroxypropylpolyethylene glycol dodecyl ether)cellulose and (laureth-13 PG-hydroxyethylcellulose)

(A-2) is preferably hydroxyethyl(hydroxypropylpolyethylene glycol dodecyl ether)cellulose or (laureth-13 PG-hydroxyethylcellulose) from the viewpoint of obtaining a clean feeling.

(G-3) A polyether polycarbonate having a constitutional unit represented by formula (2):

wherein $A^2$ represents an alkylene group having 2 to 6 carbon atoms; n represents a number of 5 to 1,000 on average; p represents a number of 5 to 100 on average; and A2, having a number of (n×p) units, are identical or different.

In formula (2), $A^2$ represents an alkylene group having 2 to 6 carbon atoms, and $A^2$, having a number of (n×p) units, are identical or different and are preferably at least two or more alkylene groups. $A^2$ is preferably an alkylene group having 2 to 4 carbon atoms, more preferably an alkylene group having 2 or 3 carbon atoms and further preferably a mixed group of an ethylene group and a propylene group. In the case of different alkyleneoxy groups, these groups may have a block structure or a random structure and more preferably have a random structure.

In formula (2), n is a number of 5 to 1,000 indicating the average addition molar number of alkyleneoxy groups and is preferably a number of 10 to 500. p is a number of 5 to 100 indicating the average number of repeats of the $[(A^2O)_n COO]$ group and is preferably a number of 5 to 50.

The weight-average molecular weight of the polyether polycarbonate is preferably 50,000 or larger, more preferably 100,000 or larger, further preferably 150,000 or larger and particularly preferably 200,000 or larger, from the viewpoint of cleansing properties. The weight-average molecular weight of the polyether polycarbonate is preferably 1,000,000 or smaller, more preferably 700,000 or smaller and further preferably 500,000 or smaller, from the viewpoint of cleansing properties.

The polyether polycarbonate as the component (G-3) can be manufactured by a method described in, for example, JP-A-2009-41004, and a compound of Synthesis Example 1, 2, or 3 described in JP-A-2009-41004 can be used.

(G-3) is preferably a compound of Synthesis Example 1, 2, or 3 described in JP-A-2009-41004 from the viewpoint of obtaining a clean feeling.

The component (G) is preferably (G-1) and more preferably (G-1) which is a copolymer comprising (g1), (g2), and (g3) as constitutional units and comprising 10 mol % or more of the monomer unit (g2) based on the total monomers and further preferably (acrylates/steareth-20 methacrylate) copolymer, (acrylates/steareth-20 methacrylate) crosspolymer, or (acrylates/beheneth-25 methacrylate) copolymer, from the viewpoint of obtaining a cleansing power and obtaining a clean feeling by refreshing the skin after cleansing.

One or two or more in combination of the components (G) can be used. The content thereof in the total composition is 0.001% by mass or more, preferably 0.005% by mass or more, more preferably 0.1% by mass or more and further preferably 0.3% by mass or more, and is 5% by mass or less, preferably 4% by mass or less, more preferably 3% by mass or less and further preferably 2% by mass or less, from the viewpoint of cleansing performance and a clean feeling of the skin after wiping. The content of the component (G) in the total composition is 0.001 to 5% by mass, preferably 0.005 to 4% by mass, more preferably 0.1 to 3% by mass and further preferably 0.3 to 2% by mass.

In the present invention, the mass ratio of the component (G) in the total oil-phase components ((G)/total oil-phase components) is preferably 0.001 or more, more preferably 0.003 or more and further preferably 0.005 or more, and is preferably 2 or less, more preferably 1 or less and further preferably 0.5 or less, from the viewpoint of cleansing performance and a duration of a smooth feel of the skin after cleansing. The mass ratio of the component (G) in the total oil-phase components ((G)/total oil-phase components) is preferably 0.001 to 2, more preferably 0.003 to 1 and further preferably 0.005 to 0.5.

The polymer as the component (H) is a polymer other than the component (G-1) and comprises acrylic acid or methacrylic acid as a constituent.

The component (H) is not limited as long as the component (H) comprises a monomer selected from the group consisting of acrylic acid and methacrylic acid. The component (H) may be a copolymer further containing other monomers and may have a cross-linked structure.

The copolymer is preferably a copolymer comprising the monomer selected from the group consisting of acrylic acid and methacrylic acid as well as a monomer selected from the group consisting of an acrylic acid alkyl ester and a methacrylic acid alkyl ester and is not limited by its content ratio or binding pattern such as a block bond or a random bond.

In this context, in the acrylic acid alkyl ester and the methacrylic acid alkyl ester, the alkyl group of the alkyl ester preferably has 1 to 22 carbon atoms and more preferably 1 to 18 carbon atoms.

Examples of the polymer as the component (H) include carboxyvinyl polymer, acrylic acid/methacrylic acid copolymer, and acrylic acid/alkyl methacrylate copolymer.

A commercially available product can be used, for example, Carbopol 980, Carbopol 981, or Carbopol ULTREZ10 (all manufactured by Lubrizol Advanced Materials) as the carboxyvinyl polymer; or PEMULEN TR-1, PEMULEN TR-2, Carbopol ETD2020, Carbopol ULTREZ20, or Carbopol ULTREZ21 (all manufactured by Lubrizol Advanced Materials) as the acrylic acid/alkyl methacrylate copolymer.

The component (H) is preferably carboxyvinyl polymer or acrylic acid/alkyl methacrylate copolymer from the viewpoint of stability.

One or two or more in combination of the components (H) can be used. The content thereof in the total composition is 0.001% by mass or more, preferably 0.005% by mass or more and more preferably 0.01% by mass or more, from the viewpoint of cleansing performance and durations of smoothness and softness of the skin after cleansing, and is 1% by mass or less, preferably 0.7% by mass or less and more preferably 0.5% by mass or less, from the viewpoint of cleansing properties for oil-based mascara. The content of the component (H) in the total composition is 0.001 to 1% by mass, preferably 0.005 to 0.7% by mass and more preferably 0.01 to 0.5% by mass.

In the present invention, the mass ratio between the components (G) and (H), (G)/(H) is 0.1 or more, preferably 0.3 or more and more preferably 0.6 or more, and is 150 or less, preferably 120 or less and more preferably 80 or less, from the viewpoint of smoothness of the skin after cleansing and a clean feeling of the skin after cleansing. The mass ratio between the components (G) and (H), (G)/(H) is 0.1 to 150, preferably 0.3 to 120 and more preferably 0.6 to 80.

In the present invention, the mass ratio of the total of the components (G) and (H) in the total oil-phase components, specifically, the mass ratio of the total content of the components (G) and (H) to the total content of the total oil-phase components, (((G)+(H))/total oil-phase components) is preferably 0.001 or more, more preferably 0.005 or more and further preferably 0.01 or more, and is preferably 2 or less, more preferably 1 or less and further preferably 0.5 or less, from the viewpoint of cleansing performance and stability. The mass ratio of the component (G) in the total oil-phase components, ((G)/total oil-phase components) is preferably 0.001 to 2, more preferably 0.005 to 1 and further preferably 0.01 to 0.5.

The viscosity at 30° C. of the hydrocarbon oil as the component (I) is 18 mPa·s or lower, preferably 15 mPa·s or lower and more preferably 10 mPa·s or lower, and is preferably 1 mPa·s or more. In this context, the viscosity was measured using a BM-type viscometer (manufactured by Tokimec, Inc., TVB-10-type viscometer, measurement conditions: rotor No. 1, 60 rpm).

Examples of the component (I) include liquid isoparaffins such as light liquid isoparaffin and hydrogenated polyisobutene, isododecane, and isohexadecane. Among them, light liquid isoparaffin, isododecane, and isohexadecane are preferred from the viewpoint of obtaining a high cleansing power and a smooth skin feel.

One or two or more in combination of the components (I) can be used. The content thereof in the total composition is 0.5% by mass or more, preferably 1% by mass or more and more preferably 4% by mass or more, and is 30% by mass or less, preferably 20% by mass or less and more preferably 15% by mass or less, from the viewpoint of cleansing performance and a cleansing feeling of the skin after application. The content of the component (I) in the total composition is 0.5 to 30% by mass, preferably 1 to 20% by mass and more preferably 4 to 15% by mass.

The content of water as the component (J) in the total composition is 40% by mass or more, preferably 50% by mass or more and more preferably 60% by mass or more, and is 98% by mass or less, preferably 90% by mass or less and more preferably 85% by mass or less, from the viewpoint of a fresh feeling of the skin and cleansing performance. The content of water as the component (J) in the total composition is 40 to 98% by mass, preferably 50 to 90% by mass and more preferably 60 to 85% by mass.

The nonionic surfactant as the component (K) used in the present invention preferably has HLB of 3 to 20 and more preferably HLB of 4 to 18.

In this context, HLB refers to an index which indicates a hydrophilic-lipophilic balance. In the present invention, a value calculated using the following expression of Oda, Teramura, etc. is used:

$$HLB = \frac{\sum \text{Inorganic value}}{\sum \text{Organic value}} \times 10$$

Examples of the component (K) include polyglycerin fatty acid ester, polyethylene glycol fatty acid ester, polyoxyethylene glycerin fatty acid ester, polyoxyethylene polyoxypropylene glycol, polyoxyethylene sorbitan fatty acid ester, polyoxyethylene sorbit fatty acid ester, polyoxyethylene castor oil, polyoxyethylene hydrogenated castor oil, polyoxyethylene hydrogenated castor oil fatty acid ester, polyoxyethylene alkyl ether, polyoxyethylene alkyl ether fatty acid ester, sucrose fatty acid ester, sorbitan fatty acid ester, alkyl polyglucoside, and (poly)alkyl glyceryl ether. Among them, polyglycerin fatty acid ester, polyethylene glycol fatty acid ester, polyoxyethylene glycerin fatty acid ester, polyoxyethylene sorbitan fatty acid ester, polyoxyethylene hydrogenated castor oil, polyoxyethylene alkyl ether, and sorbitan fatty acid ester are preferred from the viewpoint of stability.

The composition comprises no component (K), or one or two or more in combination, if any. The content thereof in the total composition is preferably 0.01% by mass or more, more preferably 0.02% by mass or more and further preferably 0.04% by mass or more, and is preferably 5% by mass or less, more preferably 2% by mass or less and further preferably 0.5% by mass or less, from the viewpoint of obtaining stability, a fresh feeling of the skin after cleansing, and high cleansing performance. The content of the component (K) in the total composition is preferably 0.01 to 5% by mass, more preferably 0.02 to 2% by mass and further preferably 0.04 to 0.5% by mass.

The skin cleansing composition of the present invention can further comprise (L) an ether oil which can thereby enhance a cleansing power and softness of the skin after cleansing.

The ether oil is preferably a dialkyl ether oil, more preferably a dialkyl ether oil comprising an alkyl group having 18 or less carbon atoms and further preferably a dialkyl ether oil comprising an alkyl group having 13 or less carbon atoms, from the viewpoint of smoothness of the skin during cleansing.

Specific examples thereof include dilauryl ether, dioctyl ether, and cetyl-1,3-dimethylbutyl ether. Dioctyl ether is preferred from the viewpoint of quickly removing oil-based mascara.

One or two or more in combination of the components (L) can be used. The content thereof in the total composition is preferably 0.5% by mass or more, more preferably 1% by mass or more and further preferably 2% by mass or more, and is preferably 20% by mass or less, more preferably 15% by mass or less and further preferably 10% by mass or less, from the viewpoint of obtaining a high cleansing power. The content of the component (L) in the total composition is preferably 0.5 to 20% by mass, more preferably 1 to 15% by mass and further preferably 2 to 10% by mass.

The skin cleansing composition of the present invention can further comprise (M) a silicone oil having a viscosity of 15 mPa·s or lower, preferably 10 mPa·s or lower, 1 mPa·s or more at 30° C. which can thereby facilitate drying the skin after cleansing.

In this context, the viscosity was measured using a BM-type viscometer (manufactured by Tokimec, Inc., TVB-10-type viscometer, measurement conditions: rotor No. 1, 60 rpm).

Examples of the component (M) include: dimethylpolysiloxane having a viscosity of 2 cs, 5 cs, or 10 cs; dimethylcyclopolysiloxanes such as octamethylcyclotetrasiloxane and decamethylcyclopentasiloxane; and methylphenylpolysiloxane. Among them, dimethylpolysiloxane having a viscosity of 2 cs, octamethylcyclotetrasiloxane, and decamethylcyclopentasiloxane are preferred, and dimethylpolysiloxane having a viscosity of 2 cs is more preferred, from the viewpoint of obtaining a feeling of quick drying after cleansing.

One or two or more in combination of the components (M) can be used. The content thereof in the total composition is preferably 0.5% by mass or more, more preferably 1% by mass or more and further preferably 2% by mass or more, and is preferably 20% by mass or less, more preferably 10% by mass or less and further preferably 6% by mass or less, from the viewpoint of cleansing performance and a fresh feeling. The content of the component (M) in the total composition is preferably 0.5 to 20% by mass, more preferably 1 to 10% by mass and further preferably 2 to 6% by mass.

In the present invention, the total content of the components (I), (L), and (M) in the total composition is preferably 1.5% by mass or more, more preferably 3% by mass or more and further preferably 8% by mass or more, and is preferably 50% by mass or less, more preferably 40% by mass or less and further preferably 30% by mass or less, from the viewpoint of cleansing performance and the absence of stickiness after cleansing. The total content of the components (I), (L), and (M) in the total composition is preferably 1.5 to 50% by mass, more preferably 3 to 40% by mass and further preferably 8 to 30% by mass.

The skin cleansing composition of the present invention can further contain (N) a polyol. Examples of the polyol include polyhydric alcohols, polyglycerin, polyethylene glycol, polypropylene glycol, and sugars.

More specifically, examples of the polyhydric alcohols include ethylene glycol, propylene glycol, isoprene glycol, 1,3-butylene glycol, hexylene glycol, trimethylolpropane, glycerin, and PPG-9 diglyceryl. Among them, propylene glycol, isoprene glycol, 1,3-butylene glycol, hexylene glycol, and glycerin are preferred, and, 1,3-butylene glycol, propylene glycol, isoprene glycol, and glycerin are more preferred from the viewpoint of a moist feeling of the skin after wiping.

Examples of the polyglycerin, the polyethylene glycol, and the polypropylene glycol include polyglycerin having a molecular weight of 2,000 or smaller, polyethylene glycol having a molecular weight of 10,000 or smaller, and polypropylene glycol having a molecular weight of 1,000 or smaller. Among them, diglycerin, polyethylene glycol 200, polyethylene glycol 400, polyethylene glycol 1,000, polyethylene glycol 1,540, dipropylene glycol, polypropylene glycol (3), and polypropylene glycol (7) are preferred from the viewpoint of a moist feeling of the skin after wiping.

Examples of the sugars include sorbitol, erythritol, pentaerythritol, methyl glucoside, ethyl glucoside, polyoxyethylene methyl glucoside, and polyoxypropylene methyl glucoside, and the like. Alkyl glucoside with an alkyl chain having 2 carbon atoms or less is preferred. Among them, methyl glucoside, ethyl glucoside, polyoxyethylene methyl glucoside, and polyoxypropylene methyl glucoside are preferred, and polyoxyethylene methyl glucoside and polyoxypropylene methyl glucoside are more preferred, from the viewpoint of a moist feeling of the skin after wiping.

One or two or more in combination of the components (N) can be used. The content thereof in the total composition is preferably 0.1% by mass or more, more preferably 0.5% by mass or more and further preferably 1% by mass or more, and is preferably 45% by mass or less, more preferably 35% by mass or less and further preferably 25% by mass or less, from the viewpoint of a moist feeling and reduction in stickiness. The content of the component (N) in the total composition is preferably 0.1 to 45% by mass, more preferably 0.5 to 35% by mass and further preferably 1 to 25% by mass.

The skin cleansing composition of the present invention can contain, in addition to the components mentioned above, those components used in usual cleansing compositions to the extent not inhibiting the effects of the present invention. The cleansing composition of the present invention can contain, for example, an oil agent other than the components (I), (L), and (M), an anionic surfactant, a cationic surfactant, an amphoteric surfactant, a bactericide, an anti-inflammatory agent, an antiseptic, a chelating agent, a salt, a pearling agent, a fragrance, a cooling agent, a dye, an ultraviolet absorber, an antioxidant, and a plant extract, and the like.

Examples of the oil agent other than the components (I), (L), and (M) include an ester oil in a liquid state at 30° C., a hydrocarbon oil (e.g., liquid paraffin) or a plant oil in a liquid state having a viscosity exceeding 18 mPa·s at 30° C., a fat in a paste or wax state at 30° C., and the like.

Examples of the ester oil in a liquid state at 30° C. include isopropyl myristate (6.6 mPa·s), isopropyl palmitate (10 mPa·s), isononyl isononanoate (9 mPa·s), neopentyl glycol dicaprate (19 mPa·s), and tri(caprylic acid/capric acid)glyceryl (26 mPa·s). The ester oil preferably has a viscosity of 30 mPa·s or lower and more preferably 15 mPa·s or lower, at 30° C. Isopropyl myristate, isopropyl palmitate, and isononyl isononanoate are preferred from the viewpoint of cleansing properties. One ester oil in a liquid state at 30° C. or two or more thereof can be used. The content thereof in the total composition is preferably 0.5% by mass or more, more preferably 1% by mass or more and further preferably 2% by mass or more, and is preferably 20% by mass or less, more preferably 15% by mass or less and further preferably 10% by mass or less. When the composition further comprises an ester oil having a viscosity exceeding 30 mPa·s, the mass ratio of the content of the ester oil having a viscosity exceeding 30 mPa·s to the content of the component (G) is preferably ½ or less, more preferably ¼ or less and further preferably 1/10 or less, from the viewpoint of cleansing properties.

Examples of the hydrocarbon oil (e.g., liquid paraffin) or the plant oil in a liquid state having a viscosity exceeding 18 mPa·s at 30° C. include liquid paraffin (22.5 mPa·s) and jojoba oil (46 mPa·s), and the like. One or two or more of these oils can be contained therein. Hydrogenated polyisobutene and liquid paraffin are preferred from the viewpoint of cleansing properties. The content of the hydrocarbon oil (e.g., liquid paraffin) or the plant oil in a liquid state having a viscosity exceeding 18 mPa·s at 30° C. in the total composition is preferably 0.5% by mass or more, more preferably 1% by mass or more and further preferably 2% by mass or more, and is preferably 60% by mass or less, more preferably 50% by mass or less and further preferably 45% by mass or less.

One or two or more in combination of the fats in a paste or wax state at 30° C. can be used. The content thereof in the total composition is preferably 0.01% by mass or more, and is preferably 1% by mass or less, more preferably 0.5% by mass or less and further preferably 0.1% by mass or less.

The mass ratio of the total content of the fat in a paste or wax state at 30° C. to the content of the component (G) is preferably 1/10 or less, more preferably 1/20 or less and further preferably 1/30 or less, from the viewpoint of cleansing properties.

The content of the anionic surfactant, the cationic surfactant, and the amphoteric surfactant in the total composition is preferably 1% by mass or less, more preferably 0.5% by mass or less, further preferably 0.1% by mass or less, and the composition is even further preferably free from these surfactants.

The content of the ultraviolet absorber in the total composition is preferably 1% by mass or less, more preferably 0.5% by mass or less, further preferably 0.1% by mass, and the composition is even further preferably free from the ultraviolet absorber.

The skin cleansing composition of the present invention can be prepared by mixing the components mentioned above by an ordinary method. The composition comprising a starting material which is solid at normal temperature can be prepared by thermally melting the solid material or dissolving the solid material in other components and then uniformly mixing all components.

The skin cleansing composition of the present invention preferably has a viscosity of 100 to 9,000 mPa·s and more preferably 1,000 to 7,000 mPa·s, at 30° C. from the viewpoint of stability and the absence of a sticky feeling during cleansing.

The viscosity is measured using a BM-type viscometer (manufactured by Tokimec, Inc., TVB-10-type viscometer, measurement conditions: rotor No. 1, 60 rpm).

The skin cleansing composition of the present invention is suitable, for example, as a facial wash, a cleansing agent, or the like and more preferably a cleansing agent. The composition is preferably used for cleansing a makeup cosmetic applied on the face.

The skin cleansing composition of the present invention can be used by, for example, a method of applying the composition on a cotton etc. and wiping the skin with the cotton etc., where the composition may be used as it is or after shaking it up till uniform if it is a separated composition; a method of wiping with a cotton etc. after applying the composition to the skin with a hand; a method of washing off after applying the composition to the skin with a hand; a method of washing after dipping the composition to a cotton etc. and applying the composition on the skin; a method of washing off after wiping the skin according to any one of the above methods. The composition can be also used in a form in which a sheet is impregnated with the composition. The composition can be used, preferably by a method of applying the composition on a cotton etc. and wiping the skin with the cotton or the like and more preferably by a method of wiping with a cotton etc. after applying the composition to the skin with a hand.

In relation to the embodiments mentioned above, the present invention further discloses the following compositions:

<1> A cleansing composition comprising the following components (A), (B), and (C):
(A) 0.001 to 5% by mass of a polymer selected from the group consisting of (A-1), (A-2), and (A-3):
 (A-1) a copolymer comprising monomers selected from the group consisting of (a1), (a2), and (a3) as constitutional units:
 (a1) a monomer selected from the group consisting of acrylic acid and methacrylic acid,
 (a2) a monomer selected from the group consisting of an acrylic acid alkyl ester and a methacrylic acid alkyl ester, and (a3) a monomer selected from the group consisting of a polyoxyethylene alkyl ester of acrylic acid and a polyoxyethylene alkyl ester of methacrylic acid, and comprising 10 mol % or more of (a2) as represented by mol % based on the total monomers;

(A-2) a polysaccharide derivative having a polyoxyalkylene chain having an average molecular weight of 300 to 100,000 and having a constitutional unit represented by formula (1):

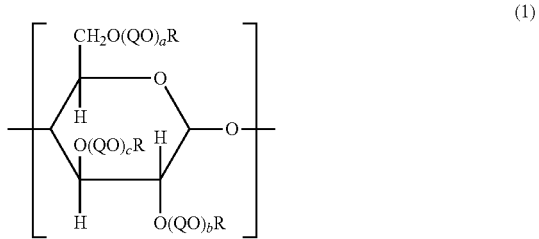

wherein R identically or differently represents a group selected from the group consisting of (d) a hydrogen atom, a methyl group, an ethyl group, a hydroxyethyl group, and a hydroxypropyl group, (e) a substituent comprising a polyoxyalkylene group, (f) a sulfoalkyl group, (g) a carboxyalkyl group, and (h) a cationic substituent; Q identically or differently represents an alkylene group having 2 to 4 carbon atoms; a, b, and c identically or differently represent a number of 0 to 10; the QO groups, the R groups, or the numbers a, b, and c are identical or different in each repeating unit or between repeating units; and when each of the substituents (e) to (h) has a hydroxy group, the hydroxy group is optionally further substituted by any of other substituents (e) to (h), provided that at least one or more substituents (e) exist as R; and (A-3) a polyether polycarbonate having a constitutional unit represented by formula (2):

wherein $A^2$ represents an alkylene group having 2 to 6 carbon atoms; n represents a number of 5 to 1,000 on average; p represents a number of 5 to 100 on average; and $A^2$, having a number of (n×p) units, are identical or different;

(B) 1 to 50% by mass of one or two or more oil agents selected from the group consisting of (b1) and (b2):

(b1) an ether oil and (b2) a hydrocarbon oil having a viscosity of 18 mPa·s or lower at 30° C.; and (C) water, and comprising (D) no nonionic surfactant having HLB of 8 or more or less than 5% by mass of the nonionic surfactant.

<2> The cleansing composition according to <1>, wherein the component (A) is (A-1) which is a copolymer comprising (a1), (a2), and (a3) as constitutional units:

(a1) a monomer selected from the group consisting of acrylic acid and methacrylic acid, (a2) a monomer selected from the group consisting of an acrylic acid alkyl ester and a methacrylic acid alkyl ester, and (a3) a monomer selected from the group consisting of a polyoxyethylene alkyl ester of acrylic acid and a polyoxyethylene alkyl ester of methacrylic acid and comprising 10 mol % or more of (a2) as represented by mol % based on the total monomers.

<3> The cleansing composition according to <1> or <2>, wherein the component (A) is (A-1) which is a copolymer comprising as constitutional units:

(a1) a monomer selected from the group consisting of acrylic acid and methacrylic acid, (a2) a monomer selected from the group consisting of alkyl esters: an acrylic acid alkyl ester and a methacrylic acid alkyl ester, wherein the alkyl group preferably has 1 to 22 carbon atoms and more preferably 1 to 18 carbon atoms, and (a3) a monomer selected from the group consisting of a polyoxyethylene alkyl ester of acrylic acid and a polyoxyethylene alkyl ester of methacrylic acid, wherein the addition molar number of polyoxyethylene is preferably 10 to 30 and more preferably 12 to 25, and the alkyl group of the alkyl ester preferably has 12 to 22 carbon atoms and more preferably 18 to 22 carbon atoms and comprising 10 mol % or more of (a2) as represented by mol % based on the total monomers.

<4> The cleansing composition according to any one of <1> to <3>, wherein the component (A) is (A-1) which is a copolymer comprising as constitutional units:

(a1) a monomer selected from the group consisting of acrylic acid and methacrylic acid, (a2) a monomer selected from the alkyl ester group consisting of an acrylic acid alkyl ester and a methacrylic acid alkyl ester, wherein the alkyl group has preferably 1 to 22 carbon atoms and more preferably 1 to 18 carbon atoms, and (a3) a monomer selected from the group consisting of a polyoxyethylene alkyl ester of acrylic acid and a polyoxyethylene alkyl ester of methacrylic acid, preferably ester of acrylic acid and polyoxyethylene (20) stearyl ether, ester of methacrylic acid and polyoxyethylene (20) stearyl ether, ester of acrylic acid and polyoxyethylene (25) behenyl ether, and ester of methacrylic acid and polyoxyethylene (25) behenyl ether and comprising 10 mol % or more of (a2) as represented by mol % based on the total monomers.

<5> The cleansing composition according to any one of <1> to <4>, wherein the component (A) is selected from the group consisting of (acrylates/steareth-20 methacrylate) copolymer, (acrylates/steareth-20 methacrylate) crosspolymer, and (acrylates/beheneth-25 methacrylate) copolymer.

<6> The cleansing composition according to any one of <1> to <5>, wherein the content of the component (A) in the total composition is preferably 0.001% by mass or more, more preferably 0.005% by mass or more, further preferably 0.01% by mass or more and even further preferably 0.03% by mass or more, and is preferably 5% by mass or less, more preferably 3% by mass or less, further preferably 2% by mass or less, and the content of the component (A) in the total composition is preferably 0.001 to 5% by mass, more preferably 0.005 to 3% by mass, further preferably 0.01 to 2% by mass and even further preferably 0.03 to 2% by mass.

<7> The cleansing composition according to any one of <1> to <6>, wherein the ether oil (b1) as the component (B) is preferably cetyl-1,3-dimethylbutyl ether, dicaprylyl ether, dicapryl ether, dilauryl ether, or diisostearyl ether and more preferably cetyl-1,3-dimethylbutyl ether or dicaprylyl ether.

<8> The cleansing composition according to any one of <1> to <7>, wherein the content of the component (b1) in the total composition is preferably 1% by mass or more, more preferably 3% by mass or more and further preferably 5% by mass or more, and is preferably 50% by mass or less, more preferably 30% by mass or less and further preferably 15% by mass or less, and the content of the component (b1) in the total composition is preferably 1 to 50% by mass, more preferably 3 to 30% by mass and further preferably 5 to 15% by mass.

<9> The cleansing composition according to any one of <1> to <8>, wherein the mass ratio of the component (b1) to the component (A), (b1)/(A) is preferably 0.5 or more, more preferably 1 or more, further preferably 2 or more and even further preferably 3 or more, and is preferably 400 or less, more preferably 300 or less and further preferably 200 or less, and the mass ratio of the component (b1) to the component (A), (b1)/(A) is preferably 0.5 to 400, more preferably 1 to 300, further preferably 2 to 200 and even further preferably 3 to 200.

<10> The cleansing composition according to any one of <1> to <9>, wherein the hydrocarbon oil (b2) as the component (B) preferably has a viscosity of 10 mPa·s or lower at 30° C.

<11> The cleansing composition according to any one of <1> to <10>, wherein the component (b2) is preferably light liquid isoparaffin, hydrogenated polyisobutene, isododecane, or isohexadecane, more preferably light liquid isoparaffin, isododecane, or isohexadecane.

<12> The cleansing composition according to any one of <1> to <11>, wherein the content of the component (b2) in the total composition is preferably 1% by mass or more, more preferably 3% by mass or more and further preferably 4% by mass or more, and is preferably 50% by mass or less, more preferably 40% by mass or less and further preferably 30% by mass or less, and the content of the component (b2) in the total composition is preferably 1 to 50% by mass, more preferably 3 to 40% by mass and further preferably 4 to 30% by mass.

<13> The cleansing composition according to any one of <1> to <12>, wherein the mass ratio of the component (b2) to the component (A), (b2)/(A) is preferably 0.5 or more, more preferably 1 or more and further preferably 2 or more, and is preferably 400 or less, more preferably 300 or less and further preferably 200 or less, and the mass ratio of the component (b2) to the component (A), (b2)/(A) is preferably 0.5 to 400, more preferably 1 to 300 and further preferably 2 to 200.

<14> The cleansing composition according to any one of <1> to <13>, wherein the content of the component (b2) is preferably an amount exceeding 35% by mass, more preferably 40% by mass or more, in the total oil agents except for (b1).

<15> The cleansing composition according to any one of <1> to <14>, wherein when the components (b1) and (b2) are used in combination, the mass ratio between the components (b1) and (b2), (b1)/(b2) is preferably 0.05 or more, more preferably 0.1 or more and further preferably 0.3 or more, and is preferably 30 or less, more preferably 10 or less and further preferably 3.5 or less, and the mass ratio between the components (b1) and (b2), (b1)/(b2) is preferably 0.05 to 30, more preferably 0.1 to 10 and further preferably 0.3 to 3.5.

<16> The cleansing composition according to any one of <1> to <15>, wherein the total content of the components (b1) and (b2) used in combination as the components (B) in the total composition is preferably 1% by mass or more, more preferably 3% by mass or more, further preferably 4% by mass or more and even further preferably 9% by mass or more, and is preferably 50% by mass or less, more preferably 40% by mass or less and further preferably 30% by mass or less, and the total content of the components (B) in the total composition is preferably 1 to 50% by mass, more preferably 3 to 40% by mass, further preferably 4 to 30% by mass and even further preferably 9 to 30% by mass.

<17> The cleansing composition according to any one of <1> to <16>, wherein the mass ratio of the component (B) to the component (A), (B)/(A) is preferably 0.5 or more, more preferably 1 or more and further preferably 2 or more, and is preferably 400 or less, more preferably 300 or less and further preferably 200 or less, and the mass ratio of the component (B) to the component (A), (B)/(A) is preferably 0.5 to 400, more preferably 1 to 300 and further preferably 2 to 200.

<18> The cleansing composition according to any one of <1> to <17>, wherein the component (D) is preferably a nonionic surfactant having HLB of 8 to 15.

<19> The cleansing composition according to any one of <1> to <18>, wherein preferred examples of the component (D) include polyglycerin fatty acid ester, polyethylene glycol fatty acid ester, polyoxyethylene glycerin fatty acid ester, polyoxyethylene polyoxypropylene glycol, polyoxyethylene sorbitan fatty acid ester, polyoxyethylene sorbit fatty acid ester, polyoxyethylene castor oil, polyoxyethylene hydrogenated castor oil, polyoxyethylene hydrogenated castor oil fatty acid ester, polyoxyethylene alkyl ether, polyoxyethylene alkyl ether fatty acid ester, sucrose fatty acid ester, alkyl polyglucoside, and (poly)alkyl glyceryl ether, and the component (D) is more preferably polyglycerin fatty acid ester, polyethylene glycol fatty acid ester, polyoxyethylene glycerin fatty acid ester, polyoxyethylene sorbitan fatty acid ester, or polyoxyethylene hydrogenated castor oil fatty acid ester.

<20> The cleansing composition according to any one of <1> to <19>, wherein the content of the component (D) in the total composition is preferably 0.05% by mass or more and more preferably 0.1% by mass or more, and is preferably 2% by mass or less and more preferably 1% by mass or less, and the content of the component (D) in the total composition is preferably 0.05 to 2% by mass and more preferably 0.1 to 1% by mass.

<21> The cleansing composition according to any one of <1> to <20>, wherein the composition may further comprise (E) a polyol.

<22> The cleansing composition according to <21>, wherein the polyol as the component (E) is preferably a polyhydric alcohol and more preferably ethylene glycol, propylene glycol, isoprene glycol, 1,3-butylene glycol, hexylene glycol, trimethylolpropane, or glycerin, further preferably propylene glycol, isoprene glycol, 1,3-butylene glycol, hexylene glycol, or glycerin and even further preferably 1,3-butylene glycol, propylene glycol, isoprene glycol, or glycerin.

<23> The cleansing composition according to <21>, wherein the polyol as the component (E) is preferably polyglycerin, polyethylene glycol, or polypropylene glycol, more preferably polyglycerin having a molecular weight of 2,000 or smaller, polyethylene glycol having a molecular weight of 10,000 or smaller, or polypropylene glycol having a molecular weight of 1,000 or smaller and further preferably diglycerin, polyethylene glycol 200, polyethylene glycol 400, polyethylene glycol 1000, polyethylene glycol 1540, dipropylene glycol, polypropylene glycol (3), or polypropylene glycol (7).

<24> The cleansing composition according to <21>, wherein the polyol as the component (E) is preferably a sugar, more preferably sorbitol, erythritol, pentaerythritol, methyl glucoside, ethyl glucoside, polyoxyethylene methyl glucoside, or polyoxypropylene methyl glucoside, further preferably alkyl glucoside with an alkyl chain having 2 or less carbon atoms, even further preferably methyl glucoside, ethyl glucoside, polyoxyethylene methyl glucoside, or polyoxypropylene methyl glucoside and still even further preferably polyoxyethylene methyl glucoside or polyoxypropylene methyl glucoside.

<25> The cleansing composition according to any one of <21> to <24>, wherein the content of the component (E) in the total composition is preferably 0.1 to 30% by mass, more preferably 0.5 to 20% by mass and further preferably 1 to 15% by mass.

<26> The cleansing composition according to any one of <1> to <25>, further comprising (F) ethanol.

<27> The cleansing composition according to <26>, wherein the content of the component (F) in the total composition is preferably 0.1 to 30% by mass, more preferably 0.5 to 20% by mass and further preferably 1 to 15% by mass.

<28> The cleansing composition according to any one of <1> to <27>, further comprising a hydrocarbon oil, such as liquid paraffin, having a viscosity exceeding 18 mPa·s at 30° C. as an oil agent other than the component (B).

<29> The cleansing composition according to <28>, wherein the content of the oil agent other than the component (B) in the total composition is preferably 0.01% by mass or more, and is preferably 50% by mass or less, more preferably 40% by mass or less, further preferably 30% by mass or less and even further preferably 20% by mass or less.

<30> The cleansing composition according to any one of <1> to <29>, wherein the composition is preferably free from an anionic surfactant, a cationic surfactant, and an amphoteric surfactant.

<31> The cleansing composition according to any one of <1> to <30>, wherein the composition is suitable as a skin cleansing composition such as a facial wash or a cleansing agent and more preferably a cleansing agent, and is preferably used for cleansing a makeup cosmetic applied on the face.

<32> The cleansing composition according to any one of <1> to <31>, wherein, the cleansing composition can be used by a method of applying the composition on a cotton etc. and wiping the skin with the cotton etc., where the composition may be used as it is or after shaking it up till uniform if it is a separated composition; a method of wiping with a cotton etc. after applying the composition to the skin with a hand; a method of washing off after applying the composition to the skin with a hand; a method of washing after dipping the composition to a cotton etc. and applying the composition on the skin with the cotton etc.; a method of washing off after wiping the skin according to any one of the above methods. The composition can be further used in a form in which a sheet is impregnated with the composition. The composition can be used, preferably by a method of applying the composition on a cotton etc. and wiping the skin with the cotton etc., more preferably by a method of wiping with a cotton etc. after applying the composition to the skin with a hand.

<33> A skin cleansing composition comprising the following components (G), (H), (I), and (J):
(G) 0.001 to 5% by mass of a polymer selected from the group consisting of (G-1), (G-2), and (G-3):
(G-1) a copolymer comprising monomers selected from the group consisting of (g1), (g2), and (g3) as constitutional units:
(g1) a monomer selected from the group consisting of acrylic acid and methacrylic acid, (g2) a monomer selected from the group consisting of an acrylic acid alkyl ester and a methacrylic acid alkyl ester, and
(g3) a monomer selected from the group consisting of a polyoxyethylene alkyl ester of acrylic acid and a polyoxyethylene alkyl ester of methacrylic acid, and comprising 10 mol % or more of the monomer unit (g2) based on the total monomers;
(G-2) a polysaccharide derivative having a polyoxyalkylene chain having an average molecular weight of 300 to 100,000 and having a constitutional unit represented by formula (1):

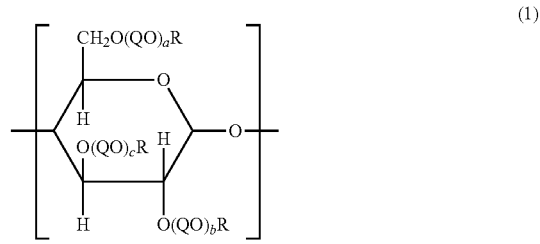

wherein R identically or differently represents a group selected from the group consisting of (d) a hydrogen atom, a methyl group, an ethyl group, a hydroxyethyl group, and a hydroxypropyl group, (e) a substituent comprising a polyoxyalkylene group, (f) a sulfoalkyl group, (g) a carboxyalkyl group, and (h) a cationic substituent; Q identically or differently represents an alkylene group having 2 to 4 carbon atoms; a, b, and c identically or differently represent a number of 0 to 10; the QO groups, the R groups, or the numbers a, b, and c are identical or different in each repeating unit or between repeating units; and when each of the substituents (e) to (h) has a hydroxy group, the hydroxy group is optionally further substituted by any of other substituents (e) to (h), provided that at least one or more substituents (e) exist as R; and
(G-3) a polyether polycarbonate having a constitutional unit represented by formula (2):

wherein $A^2$ represents an alkylene group having 2 to 6 carbon atoms; n represents a number of 5 to 1,000 on average; p represents a number of 5 to 100 on average; and $A^2$, having a number of (n×p) units, are identical or different;
(H) 0.001 to 1% by mass of a polymer comprising acrylic acid or methacrylic acid as a constituent, other than the component (G-1);
(I) 0.5 to 30% by mass of a hydrocarbon oil having a viscosity of 18 mPa·s or lower at 30° C.; and
(J) 40 to 98% by mass of water, and comprising (K) no nonionic surfactant or 5% by mass or less of the nonionic surfactant, wherein
the mass ratio between the components (G) and (H), (G)/(H) is 0.1 to 150.

<34> The skin cleansing composition according to <33>, wherein the component (G) is preferably (G-1), more preferably a copolymer comprising monomers (g1), (g2), and (g3) as constitutional units:

(g1) a monomer selected from the group consisting of acrylic acid and methacrylic acid,
(g2) a monomer selected from the group consisting of an acrylic acid alkyl ester and a methacrylic acid alkyl ester, and
(g3) a monomer selected from the group consisting of a polyoxyethylene alkyl ester of acrylic acid and a polyoxyethylene alkyl ester of methacrylic acid, and comprising 10 mol % or more of (g2) as represented by mol % based on the total monomers.

<35> The skin cleansing composition according to <33> or <34>, wherein the component (G) is preferably (G-1), more preferably (acrylates/steareth-20 methacrylate) copolymer, (acrylates/steareth-20 methacrylate) crosspolymer, or (acrylates/beheneth-25 methacrylate) copolymer.

<36> The skin cleansing composition according to <33>, wherein the component (G) is preferably (G-2), more preferably a polysaccharide derivative in which the hydrogen atoms of hydroxy groups in a polysaccharide or a derivative thereof are partially or completely replaced with (e) a substituent comprising a polyoxyalkylene group, wherein (e) is further preferably a group represented by the following formula (6):

$$-E^1-(OA^1)_q-E^2-R^6 \quad (6)$$

wherein $E^1$ represents an optionally hydroxy group- or oxo group-substituted divalent saturated hydrocarbon group having 1 to 6 carbon atoms; q represents a number of 8 to 300; $A^1$, having a number of q units, identically or differently represent a divalent saturated hydrocarbon group having 1 to 6 carbon atoms; $E^2$ represents an ether bond or an oxycarbonyl group; and $R^6$ represents an optionally hydroxy group-substituted alkyl group having 4 to 30 carbon atoms.

<37> The skin cleansing composition according to any one of <33> to <36>, wherein the content of the component (G) is preferably 0.005% by mass or more, more preferably 0.1% by mass or more and further preferably 0.3% by mass or more, and is preferably 4% by mass or less, more preferably 3% by mass or less and further preferably 2% by mass or less, and the content of the component (G) in the total composition is preferably 0.005 to 4% by mass, more preferably 0.1 to 3% by mass and further preferably 0.3 to 2% by mass.

<38> The skin cleansing composition according to any one of <33> to <37>, wherein the mass ratio of the component (G) in the total oil-phase components, ((G)/total oil-phase components) is preferably 0.001 or more, more preferably 0.003 or more and further preferably 0.005 or more, and is preferably 2 or less, more preferably 1 or less and further preferably 0.5 or less, and the mass ratio of the component (G) in the total oil-phase components, ((G)/total oil-phase components) is preferably 0.001 to 2, more preferably 0.003 to 1 and further preferably 0.005 to 0.5.

<39> The skin cleansing composition according to any one of <33> to <38>, wherein the polymer as the component (H) is preferably carboxyvinyl polymer, acrylic acid/methacrylic acid copolymer, or acrylic acid/alkyl methacrylate copolymer, more preferably carboxyvinyl polymer or acrylic acid/alkyl methacrylate copolymer.

<40> The skin cleansing composition according to any one of <33> to <39>, wherein the content of the component (H) in the total composition is preferably 0.005% by mass or more, more preferably 0.01% by mass or more, and is preferably 0.7% by mass or less, more preferably 0.5% by mass or less, and the content of the component (H) in the total composition is preferably 0.005 to 0.7% by mass, more preferably 0.01 to 0.5% by mass.

<41> The skin cleansing composition according to any one of <33> to <40>, wherein the mass ratio between the components (G) and (H), (G)/(H) is preferably 0.3 or more, more preferably 0.6 or more, and is preferably 120 or less, more preferably 80 or less, and the mass ratio between the components (G) and (H), (G)/(H) is preferably 0.3 to 120 and more preferably 0.6 to 80.

<42> The skin cleansing composition according to any one of <33> to <41>, wherein the mass ratio of the total content of the components (G) and (H) to the total content of whole oil-phase components, ((G)+(H))/whole oil-phase components) is preferably 0.001 or more, more preferably 0.005 or more and further preferably 0.01 or more, and is preferably 2 or less, more preferably 1 or less and further preferably 0.5 or less, and the mass ratio of the total content of the components (G) and (H) to the total content of whole oil-phase components, ((G)+(H)/whole oil-phase components) is preferably 0.001 to 2, more preferably 0.005 to 1 and further preferably 0.01 to 0.5.

<43> The skin cleansing composition according to any one of <33> to <42>, wherein the hydrocarbon oil as the component (I) preferably has a viscosity of 10 mPa·s or lower at 30° C. and is more preferably light liquid isoparaffin, isododecane, or isohexadecane.

<44> The skin cleansing composition according to any one of <33> to <43>, wherein the content of the component (I) in the total composition is preferably 1% by mass or more, more preferably 4% by mass or more, and is preferably 20% by mass or less, more preferably 15% by mass or less, and the content of the component (I) in the total composition is preferably 1 to 20% by mass, more preferably 4 to 15% by mass.

<45> The skin cleansing composition according to any one of <33> to <44>, wherein the content of water as the component (J) in the total composition is preferably 50% by mass or more, more preferably 60% by mass or more, and is preferably 90% by mass or less, more preferably 85% by mass or less, and the content of water as the component (J) in the total composition is preferably 50 to 90% by mass, more preferably 60 to 85% by mass.

<46> The skin cleansing composition according to any one of <33> to <45>, wherein the nonionic surfactant as the component (K) preferably has HLB of 3 to 20, more preferably HLB of 4 to 18.

<47> The skin cleansing composition according to any one of <33> to <46>, wherein the composition comprises no component (K), or when the composition comprises the component (K), the content thereof in the total composition is preferably 0.02% by mass or more, more preferably 0.04% by mass or more, and is preferably 2% by mass or less, more preferably 0.5% by mass or less, and the content of the component (K) in the total composition is preferably 0.02 to 2% by mass, more preferably 0.04 to 0.5% by mass.

<48> The skin cleansing composition according to any one of <33> to <47>, further comprising (L) an ether oil.

<49> The skin cleansing composition according to <48>, wherein the component (L) is preferably a dialkyl ether oil, more preferably a dialkyl ether oil consisting of an alkyl group having 18 or less carbon atoms and further preferably a dialkyl ether oil consisting of an alkyl group having 13 or less carbon atoms.

<50> The skin cleansing composition according to <48>, wherein the component (L) is preferably dilauryl ether, dioctyl ether, or cetyl-1,3-dimethylbutyl ether and more preferably dioctyl ether.

<51> The skin cleansing composition according to any one of <48> to <50>, wherein the content of the component (L)

in the total composition is preferably 0.5% by mass or more, more preferably 1% by mass or more and further preferably 2% by mass or more, and is preferably 20% by mass or less, more preferably 15% by mass or less and further preferably 10% by mass or less, and the content of the component (L) in the total composition is preferably 0.5 to 20% by mass, more preferably 1 to 15% by mass and further preferably 2 to 10% by mass.

<52> The skin cleansing composition according to any one of <33> to <51>, further comprising (M) a silicone oil having a viscosity of 15 mPa·s or lower and preferably 10 mPa·s or lower, at 30° C.

<53> The skin cleansing composition according to <52>, wherein the component (M) is preferably dimethylpolysiloxane having a viscosity of 2 cs, octamethylcyclotetrasiloxane, or decamethylcyclopentasiloxane, more preferably dimethylpolysiloxane having a viscosity of 2 cs.

<54> The skin cleansing composition according to <52> or <53>, wherein the content of the component (M) in the total composition is preferably 0.5% by mass or more, more preferably 1% by mass or more and further preferably 2% by mass or more, and is preferably 20% by mass or less, more preferably 10% by mass or less and further preferably 6% by mass or less, and the content of the component (M) in the total composition is preferably 0.5 to 20% by mass, more preferably 1 to 10% by mass and further preferably 2 to 6% by mass.

<55> The skin cleansing composition according to any one of <33> to <54>, wherein the total content of the components (I), (L), and (M) in the total composition is preferably 1.5% by mass or more, more preferably 3% by mass or more and further preferably 8% by mass or more, and is preferably 50% by mass or less, more preferably 40% by mass or less and further preferably 30% by mass or less, and the total content of the components (I), (L), and (M) in the total composition is preferably 1.5 to 50% by mass, more preferably 3 to 40% by mass and further preferably 8 to 30% by mass.

<56> The skin cleansing composition according to any one of <33> to <55>, further comprising (N) a polyol.

<57> The skin cleansing composition according to <56>, wherein the component (N) is preferably a polyhydric alcohol, polyglycerin, polyethylene glycol, polypropylene glycol, or a sugar.

<58> The skin cleansing composition according to <56> or <57>, wherein the content of the component (N) in the total composition is preferably 0.1% by mass or more, more preferably 0.5% by mass or more and further preferably 1% by mass or more, and is preferably 45% by mass or less, more preferably 35% by mass or less and further preferably 25% by mass or less, and the content of the component (N) in the total composition is 0.1 to 45% by mass, more preferably 0.5 to 35% by mass and further preferably 1 to 25% by mass.

<59> The cleansing composition according to any one of <33> to <58>, further comprising, for example, an ester oil in a liquid state at 30° C., a hydrocarbon oil (e.g., liquid paraffin) or a plant oil in a liquid state having a viscosity exceeding 18 mPa·s at 30° C., and a fat in a paste or wax state at 30° C. as oil agents other than the components (I), (L), and (M).

<60> The cleansing composition according to <59>, wherein the ester oil in a liquid state at 30° C. is preferably isopropyl myristate (6.6 mPa·s), isopropyl palmitate (10 mPa·s), isononyl isononanoate (9 mPa·s), neopentyl glycol dicaprate (19 mPa·s), or tri(caprylic acid/capric acid)diglyceryl (26 mPa·s), more preferably an ester oil having a viscosity of 30 mPa·s or lower, further preferably 15 mPa·s or lower, at 30° C. and even further preferably isopropyl myristate, isopropyl palmitate, or isononyl isononanoate.

<61> The cleansing composition according to <59> or <60>, wherein the content of the ester oil in a liquid state at 30° C. in the total composition is preferably 0.5% by mass or more, more preferably 1% by mass or more and further preferably 2% by mass or more, and is preferably 20% by mass or less, more preferably 15% by mass or less and further preferably 10% by mass or less.

<62> The cleansing composition according to any one of <59> to <61>, wherein when the composition comprises an ester oil having a viscosity exceeding 30 mPa·s, the mass ratio of the content of the ester oil having a viscosity exceeding 30 mPa·s to the content of the component (G) is preferably ½ or less, more preferably ¼ or less and further preferably ¹⁄₁₀ or less.

<63> The cleansing composition according to <59>, wherein the hydrocarbon oil (e.g., liquid paraffin) or the plant oil in a liquid state having a viscosity exceeding 18 mPa·s at 30° C. is preferably liquid paraffin (22.5 mPa·s) or jojoba oil (46 mPa·s), more preferably hydrogenated polyisobutene or liquid paraffin.

<64> The cleansing composition according to <59> or <63>, wherein the content of the hydrocarbon oil (e.g., liquid paraffin) or the plant oil in a liquid state having a viscosity exceeding 18 mPa·s at 30° C. in the total composition is preferably 0.5% by mass or more, more preferably 1% by mass or more and further preferably 2% by mass or more, and is preferably 60% by mass or less, more preferably 50% by mass or less and further preferably 45% by mass or less.

<65> The cleansing composition according to <59>, wherein the content of the fat in a paste or wax state at 30° C. in the total composition is preferably 0.01% by mass or more, and is preferably 1% by mass or less, more preferably 0.5% by mass or less and further preferably 0.1% by mass or less.

<66> The cleansing composition according to <59> or <65>, wherein the mass ratio of the total content of the fat in a paste or wax state at 30° C. to the content of the component (G) is preferably ¹⁄₁₀ or less, more preferably ¹⁄₂₀ or less and further preferably ¹⁄₃₀ or less.

<67> The cleansing composition according to any one of <33> to <66>, wherein the content of an anionic surfactant, a cationic surfactant, and an amphoteric surfactant in the total composition is preferably 1% by mass or less, more preferably 0.5% by mass or less, further preferably 0.1% by mass and even further preferably free from these surfactants.

<68> The cleansing composition according to any one of <33> to <67>, wherein the content of an ultraviolet absorber in the total composition is preferably 1% by mass or less, more preferably 0.5% by mass or less, further preferably 0.1% by mass and even further preferably free from the ultraviolet absorber.

<69> The cleansing composition according to any one of <33> to <68>, wherein the composition has a viscosity of preferably 100 to 9,000 mPa·s, more preferably 1,000 to 7,000 mPa·s, at 30° C.

<70> The cleansing composition according to any one of <33> to <69>, wherein the composition is suitable as a facial wash, a cleansing agent, or the like, more preferably a cleansing agent, and is preferably used for cleansing a makeup cosmetic applied on the face.

<71> The cleansing composition according to any one of <33> to <69>, wherein the cleansing composition can be used by a method of applying the composition on a cotton etc. and wiping the skin with the cotton etc., where the composition may be used as it is or after shaking it up till uniform if it is a separated composition; a method of wiping with a cotton etc. after applying the composition to the skin with a hand; a method of washing off after applying the composition to the skin with a hand; a method of washing after dipping the composition to a cotton etc. and applying the composition on the skin with the cotton etc.; a method of washing off after wiping the skin according to any one of the above methods; or a method in a form in which a sheet is impregnated with the composition; preferably a method of applying the composition on a cotton etc. and wiping the skin with the cotton etc. and more preferably by a method of wiping with a cotton etc. after applying the composition to the skin with a hand.

<72> Use of a skin cleansing composition according to any one of <33> to <71> for cleansing a cosmetic applied on the face.

<73> Use of a skin cleansing composition according to any one of <33> to <71>, wherein the composition is used for cleansing a makeup cosmetic applied on the face.

<74> Use of a skin cleansing composition according to any one of <33> to <71>, wherein the composition is used for wiping off a makeup cosmetic applied on the face.

<75> Use of a skin cleansing composition comprising the following components (G), (H), (I), and (J):

(G) 0.001 to 5% by mass of a polymer selected from the group consisting of (G-1), (G-2), and (G-3):

(G-1) a copolymer comprising monomers selected from the group consisting of (g1), (g2), and (g3) as constitutional units:

(g1) a monomer selected from the group consisting of acrylic acid and methacrylic acid, (g2) a monomer selected from the group consisting of an acrylic acid alkyl ester and a methacrylic acid alkyl ester, and (g3) a monomer selected from the group consisting of a polyoxyethylene alkyl ester of acrylic acid and a polyoxyethylene alkyl ester of methacrylic acid, and comprising 10 mol % or more of the monomer unit (g2) based on the total monomers;

(G-2) a polysaccharide derivative having a polyoxyalkylene chain having an average molecular weight of 300 to 100,000 and having a constitutional unit represented by formula (1):

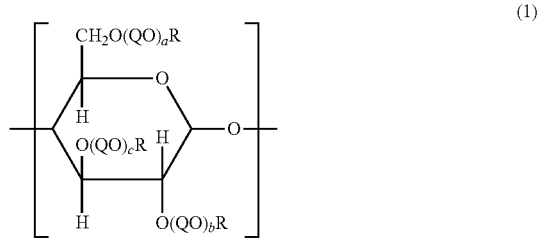

(1)

wherein R identically or differently represents a group selected from the group consisting of (d) a hydrogen atom, a methyl group, an ethyl group, a hydroxyethyl group, and a hydroxypropyl group, (e) a substituent comprising a polyoxyalkylene group, (f) a sulfoalkyl group, (g) a carboxyalkyl group, and (h) a cationic substituent; Q identically or differently represents an alkylene group having 2 to 4 carbon atoms; a, b, and c identically or differently represent a number of 0 to 10; the QO groups, the R groups, or the numbers a, b, and c are identical or different in each repeating unit or between repeating units; and when each of the substituents (e) to (h) has a hydroxy group, the hydroxy group is optionally further substituted by any of other substituents (e) to (h), provided that at least one or more substituents (e) exist as R; and (G-3) a polyether polycarbonate having a constitutional unit represented by formula (2):

(2)

wherein $A^2$ represents an alkylene group having 2 to 6 carbon atoms; n represents a number of 5 to 1,000 on average; p represents a number of 5 to 100 on average; and $A^2$, having a number of (n×p) units, are identical or different;

(H) 0.001 to 1% by mass of a polymer comprising acrylic acid or methacrylic acid as a constituent, other than the component (G-1);

(I) 0.5 to 30% by mass of a hydrocarbon oil having a viscosity of 18 mPa·s or lower at 30° C.; and (J) 40 to 98% by mass of water, and comprising (K) no nonionic surfactant or 5% by mass or less of the nonionic surfactant, wherein the mass ratio between the components (G) and (H), (G)/(H) is 0.1 to 150 for cleansing a cosmetic applied on the face.

EXAMPLES

Synthesis Example 1

(Synthesis of (Acrylic Acid/Stearyl Acrylate) Copolymer)

A reactor equipped with a dropping funnel, a stirrer, a reflux condenser, a thermometer, and a nitrogen inlet tube was charged with 1/10 of the amount of a mixed solution consisting of 67 parts of acrylic acid, 33 parts of stearyl acrylate, and 67 parts of a polymerization solvent isopropyl alcohol and the reaction temperature was raised to 75° C. The remaining portion of the mixed solution and 0.5 parts of an initiator V-65 (2,2'-azobis(2,4-dimethylvaleronitrile), manufactured by Wako Pure Chemical Industries, Ltd.) were each added dropwise thereto over a period of 2.5 hours using the dropping funnel, while the temperature in the reactor was kept at 75° C. After the completion of the dropwise addition, the reaction mixture was aged for 1 hour, and 0.2 parts of the initiator V-65 were then added thereto three times every 30 minutes. Then, the reaction temperature was raised to 80° C. After a lapse of 1 hour, the reaction was terminated. Unreacted monomers and initiator residues were removed from the reaction product using an alumina ceramic membrane purifier having a pore size of 500 Å, and the solvent was distilled off to give (acrylic acid/stearyl acrylate) copolymer as a white solid. The obtained copolymer had a weight-average molecular weight of 35,000.

Synthesis Example 2

(Synthesis of Hydroxyethyl Cellulose Derivative (Hydroxyethyl(Hydroxypropylpolyethylene Glycol Dodecyl Ether)Cellulose))

160 g of hydroxyethylcellulose (NATROZOL 250G, manufactured by Hercules Inc.) having a weight-average molecular weight of 200,000 and a substitution degree of hydroxyethyl group of 2.5, 1280 g of 80% aqueous isopropyl alcohol, and 9.8 g of a 48% aqueous sodium hydroxide solution were mixed to prepare a slurry solution, which was then stirred at room temperature for 30 minutes in a nitrogen atmosphere. To this solution, 31.8 g of a compound represented by the following formula:

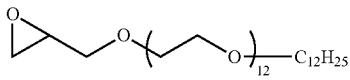

was added, and the mixture was subjected to a reaction at 80° C. for 8 hours for formation of polyoxyalkylene. After the completion of the reaction, the reaction solution was neutralized with acetic acid, and the reaction product was collected by filtration. The reaction product was washed with 700 g of isopropyl alcohol twice and then dried all night and all day at 60° C. under reduced pressure to give 152 g of a hydroxyethyl cellulose derivative having a polyoxyalkylene moiety. The substitution degree of the substituent (6) comprising a polyoxyalkylene group in the obtained hydroxyethyl cellulose derivative was 0.014.

Synthesis Example 3

Synthesis of Polyether Polycarbonate

A reaction vessel equipped with a stirrer, a fractional distillation condenser, and a thermometer was charged with 27.1 g (0.005 mol) of a random copolymer of ethylene oxide and propylene oxide (number-average molecular weight: 5,000, hydroxy value: 22.0 mg KOH/g, manufactured by ADEKA Corp., trade name: ADEKA Polyether PR-5007), 1.15 g (0.005 mol) of diphenyl carbonate, and 4 mg (0.01 mmol) of cesium carbonate.

The temperature in the reaction vessel was raised to 160° C. with stirring. In this state, heating was continued for 2 hours to discharge phenol formed through the reaction from the system. Vacuum suction was further started using a vacuum pump. While the temperature was gradually raised to 180° C., the reaction was performed for approximately 4 hours to give polyether polycarbonate. This polyether polycarbonate had a weight-average molecular weight of 180,000.

Examples 1 and 2 and Comparative Examples 1 and 2

Each skin cleansing composition was prepared according to the composition shown in Table 1 and evaluated for its cleansing power, clean feeling, and residual oil agent level. The results are also shown in Table 1.

(Production Method)

A copolymer was added to water at room temperature and the mixture was stirred for uniform mixing. Then, an ether oil was added as the component (B) to the mixture with stirring and dispersed therein, and 48% potassium hydroxide was further added thereto to give a skin cleansing composition.

(Evaluation Method)

(1) Cleansing Power for Oil-Based Mascara:

0.005 g of KOSE Sports Beauty Fasio Power Stay Mascara (Curl Long) BK001 (trade name) was uniformly applied as oil-based mascara (waterproof mascara) in a circular pattern of 1.2 cm in diameter onto slide glass and allowed to stand for 12 hours for drying. Approximately 2 g of each cleansing composition was uniformly applied on a cosmetic cotton (LILY BELL Lilian Puff/Suzuran Sanitary Goods Co., Ltd.; the same type of cosmetic cotton was used in subsequent evaluations). The cosmetic cotton was put on the oil-based mascara and lightly pressed for 10 seconds. Then, the oil-based mascara was wiped off at a given pressure (7.8 kPa). The number of wipes necessary for removing the mascara was measured.

(2) Cleansed Feeling after Wiping:

Ten female expert panelists applied each cleansing composition on a cosmetic cotton and wiped their makeup cosmetic-applied faces using the cotton. The panelists conducted sensory evaluation for a clean feeling of the skin after wiping according to five grades: "5: Good", "4: Slightly good", "3: Not good or not bad", "2: Not very good", and "1: Not good". The sum of the scores of the ten panelists was determined.

(3) Residual Oil Agent Level after Wiping:

A region of forearm was washed with a detergent for dishwashing (manufactured by Kao Corp., Kyukyutto), and moisture was wiped off with a paper towel, followed by drying at room temperature for 10 minutes. Approximately 2 g of each cleansing composition was uniformly applied on a commercially available cosmetic cotton. The region of forearm was wiped using the cosmetic cotton. Within 10 seconds, the region of forearm was loaded in a measurement apparatus where a residual oil agent level (peak area ratio of spectra: which was evaluated from the difference between the measurement value of the arm thus washed with the detergent for dishwashing and the measurement value after this test) was then determined on the basis of infrared absorption spectra. The measurement apparatus used was a Fourier transform infrared spectrophotometer (manufactured by Thermo Scientific Inc.).

TABLE 1

|   |    | Component (% by mass) | Example 1 | Example 2 | Comparative Example 1 | Comparative Example 2 |
|---|----|----|----|----|----|----|
| A |    | (Acrylates/steareth-20 methacrylate) copolymer (manufactured by Rohm and Haas Company, ACULYN 22 (solid content: 30%)) | 0.34 | 1.67 |  |  |
|   |    | Acrylic acid/alkyl (C10-30) methacrylate copolymer (manufactured by Lubrizol Advanced Materials, PEMULEN TR-2) |  |  | 0.1 |  |
|   |    | Carboxyvinyl polymer (manufactured by Lubrizol Advanced Materials, Carbopol 981) |  |  |  | 0.1 |
| B | b1 | Dicaprylyl ether (manufactured by BASF Personal Care and Nutrition GmbH, Cetiol OE) | 10 | 10 | 10 | 10 |

TABLE 1-continued

|  | Component (% by mass) | Example 1 | Example 2 | Comparative Example 1 | Comparative Example 2 |
|---|---|---|---|---|---|
| C | Water | 89.625 | 88.16 | 89.85 | 89.85 |
|   | 48% KOH | 0.035 | 0.17 | 0.05 | 0.05 |
| Total |  | 100 | 100 | 100 | 100 |
| Active amount (%) of A |  | 0.10 | 0.50 | — | — |
| b1/A |  | 98.0 | 20.0 | — | — |
| B/A |  | 98.0 | 20.0 | — | — |
| Cleansing power |  | 2 | 4 | 3 | 2 |
| Clean feeling |  | 40 | 46 | 27 | 19 |
| Residual oil agent level |  | 375 | 170 | 576 | 817 |

Examples 3 to 12 and Comparative Examples 3 to 5

Each skin cleansing composition was prepared according to the formulation shown in Table 2 and evaluated for its cleansing power and clean feeling in the same way as in Examples 1 and 2. The results are also shown in Table 2.

(Preparation Method)

A surfactant as the component (D) and a polyol as the component (E) were added according to the need to water at 80° C. The mixture was stirred for uniform mixing. A copolymer as the component (A) was added to the mixture and the mixture was stirred for uniform mixing, followed by cooling to 30° C. or lower. An oil agent as the component (B) and other oil agents were further added thereto and the mixture was stirred, and 48% potassium hydroxide and a fragrance were added thereto and stirred to give a skin cleansing composition.

When all of the components were in a liquid state at room temperature or gel-like components were not formed by mixing at room temperature, the production was carried out at room temperature.

TABLE 2

|  |  | Component (% by mass) | Example 3 | Example 4 | Example 5 | Example 6 | Example 7 | Example 8 | Example 9 |
|---|---|---|---|---|---|---|---|---|---|
| A |  | (Acrylates/steareth-20 methacrylate) copolymer (manufactured by Rohm and Haas Company, ACULYN 22 (solid content: 30%)) | 1.5 | 1.5 |  |  | 0.1 | 1.5 | 1.5 |
|  |  | (Acrylates/beheneth-25 methacrylate) copolymer (manufactured by Rohm and Haas Company, ACULYN 28 (solid content: 20%)) |  |  | 1.5 |  |  |  |  |
|  |  | (Acrylates/steareth-20 methacrylate) copolymer (manufactured by Rohm and Haas Company, ACULYN 88 (solid content: 29%)) |  |  |  | 1.5 |  |  |  |
| B | b1 | Dicaprylyl ether (manufactured by BASF Personal Care and Nutrition GmbH, Cetiol OE) | 10 | 8 |  |  |  | 10 | 6 |
|  |  | Cetyl-1,3-dimethylbutyl ether (manufactured by Kao Corp, ASE-166K) |  | 2 |  |  |  |  |  |
|  | b2 | Isododecane (5 mPa · s) |  |  | 10 |  | 5.4 |  |  |
|  |  | Light liquid isoparaffin (5 mPa · s) (manufactured by Idemitsu Kosan Co., Ltd., IP SOLVENT (IP-2028MU)) |  |  |  | 5 |  |  |  |
|  |  | Light liquid isoparaffin (5 mPa · s) (manufactured by NOF Corp., PARLEAM 4) |  | 5 |  | 5 |  |  | 14 |
| C |  | Water | 83.32 | 78.32 | 76.32 | 82.32 | 89.46 | 83.315 | 73.17 |
| D |  | Diglycerin monoisostearate (HLB: 8) (manufactured by The Nisshin Oillio Group, Ltd., COSMOL 41V) |  |  |  |  |  | 0.005 |  |
|  |  | Polyoxyethylene coconut oil fatty acid glycerin (HLB: 13) (manufactured by NOF Corp., UNIGLY MK-207G) |  |  |  |  |  |  |  |
|  |  | (PEG12) Polyethylene glycol monolaurate (HLB: 14) (manufactured by Kao Corp., EMANON 1112HG) |  |  |  |  | 1 |  |  |
|  |  | Polyoxyethylene sorbitan monostearate (HLB: 15) (manufactured by Kao Corp., RHEODOL TW-S120V) |  |  |  |  |  |  | 0.05 |
| E |  | 1,3-Butylene glycol | 5 | 5 | 5 | 5 | 5 | 5 | 5 |
|  |  | Glycerin |  |  |  | 5 |  |  |  |
| Others |  | Sorbitan monostearate (HLB: 5) (manufactured by Kao Corp., RHEODOL SP-S10V) |  |  |  |  |  |  | 0.1 |
|  |  | Decamethylcyclopentasiloxane (manufactured by Dow Corning Toray Co., Ltd., Silicone SH245) |  |  |  |  |  |  |  |
|  |  | Hydrogenated polyisobutene (16.5 mPa · s) (manufactured by NOF Corp., PARLEAM Ex) |  |  |  |  | 2 |  |  |
|  |  | Liquid paraffin (22.5 mPa · s) (manufactured by Kaneda Co., Ltd., HICALL K-230) |  |  |  |  |  |  |  |
|  |  | Squalane |  |  |  |  |  |  |  |
|  |  | Fragrance | 0.03 | 0.03 | 0.03 | 0.03 | 0.03 | 0.03 | 0.03 |
|  |  | 48% KOH | 0.15 | 0.15 | 0.15 | 0.15 | 0.01 | 0.15 | 0.15 |
|  |  | Total | 100 | 100 | 100 | 100 | 100 | 100 | 100 |
|  |  | Active amount (%) of A | 0.45 | 0.45 | 0.3 | 0.44 | 0.03 | 0.45 | 0.45 |
|  |  | Total amount (%) of B | 10 | 15 | 10 | 10 | 5.4 | 10 | 20 |
|  |  | b1/A | 22.2 | 22.2 |  |  |  | 22.2 | 13.3 |

TABLE 2-continued

| | | | | | | |
|---|---|---|---|---|---|---|
| b2/A | | 11.1 | 33.3 | 23.0 | 180 | | 31.1 |
| B/A | 22.2 | 33.3 | 33.3 | 23.0 | 180 | 22.2 | 44.4 |
| b1/b2 | | 2 | | | | | 0.4 |
| Content (% by mass) of b2 in whole oil agents except for b1 | | 100 | 83.3 | 100 | 100 | | 100 |
| Cleansing power | 10 | 12 | 9 | 18 | 16 | 10 | 6 |
| Clean feeling | 41 | 39 | 42 | 41 | 38 | 41 | 40 |

| | | | Example | | | Comparative Example | | |
|---|---|---|---|---|---|---|---|---|
| | | Component (% by mass) | 10 | 11 | 12 | 3 | 4 | 5 |
| A | | (Acrylates/steareth-20 methacrylate) copolymer (manufactured by Rohm and Haas Company, ACULYN 22 (solid content: 30%)) | 1.67 | 5 | 15 | 1.5 | | |
| | | (Acrylates/beheneth-25 methacrylate) copolymer (manufactured by Rohm and Haas Company, ACULYN 28 (solid content: 20%)) | | | | | | |
| | | (Acrylates/steareth-20 methacrylate) copolymer (manufactured by Rohm and Haas Company, ACULYN 88 (solid content: 29%)) | | | | | | |
| B | b1 | Dicaprylyl ether (manufactured by BASF Personal Care and Nutrition GmbH, Cetiol OE) | 6 | 10 | 10 | | | |
| | | Cetyl-1,3-dimethylbutyl ether (manufactured by Kao Corp, ASE-166K) | | | | | 10 | |
| | b2 | Isododecane (5 mPa · s) | | 25 | 15 | | | |
| | | Light liquid isoparaffin (5 mPa · s) (manufactured by Idemitsu Kosan Co., Ltd., IP SOLVENT (IP-2028MU)) | | | 15 | | | |
| | | Light liquid isoparaffin (5 mPa · s) (manufactured by NOF Corp., PARLEAM 4) | 1.6 | | | | | 5 |
| C | | Water | 85.55 | 50.47 | 43.5 | 83.32 | 79.97 | 64.97 |
| D | | Diglycerin monoisostearate (HLB: 8) (manufactured by The Nisshin Oillio Group, Ltd., COSMOL 41V) | | | | | | |
| | | Polyoxyethylene coconut oil fatty acid glycerin (HLB: 13) (manufactured by NOF Corp., UNIGLY MK-207G) | | 4 | | | | |
| | | (PEG12) Polyethylene glycol monolaurate (HLB: 14) (manufactured by Kao Corp., EMANON 1112HG) | | | | | | |
| | | Polyoxyethylene sorbitan monostearate (HLB: 15) (manufactured by Kao Corp., RHEODOL TW-S120V) | | | | | | |
| E | | 1,3-Butylene glycol | 5 | 5 | | 5 | | |
| | | Glycerin | | | | | 5 | 5 |
| Others | | Sorbitan monostearate (HLB: 5) (manufactured by Kao Corp., RHEODOL SP-S10V) | | | | | | |
| | | Decamethylcyclopentasiloxane (manufactured by Dow Corning Toray Co., Ltd., Silicone SH245) | | | | | | 25 |
| | | Hydrogenated polyisobutene (16.5 mPa · s) (manufactured by NOF Corp., PARLEAM Ex) | | | | | | |
| | | Liquid paraffin (22.5 mPa · s) (manufactured by Kaneda Co., Ltd., HICALL K-230) | | | | | 10 | |
| | | Squalane | | | | | 5 | |
| | | Fragrance | 0.03 | 0.03 | | 0.03 | 0.03 | 0.03 |
| | | 48% KOH | 0.15 | 0.5 | 1.5 | 0.15 | | |
| | | Total | 100 | 100 | 100 | 100 | 100 | 100 |
| | | Active amount (%) of A | 0.50 | 1.5 | 4.5 | 0.45 | | |
| | | Total amount (%) of B | 7.6 | 35 | 40 | 0 | 10 | 5 |
| | | b1/A | 12.0 | 6.7 | 2.2 | | | |
| | | b2/A | 3.2 | 16.7 | 6.7 | | | |
| | | B/A | 15.2 | 23.3 | 8.9 | | | |
| | | b1/b2 | 3.8 | 0.4 | 0.3 | | | |
| | | Content (% by mass) of b2 in whole oil agents except for b1 | 100 | 100 | 100 | | | 16.7 |
| | | Cleansing power | 13 | 3 | 4 | 31 | 24 | 48 |
| | | Clean feeling | 42 | 37 | 34 | 25 | 11 | 31 |

Examples 13 to 27

In the same way as in Examples 3 to 12, each skin cleansing composition was prepared according to the formulation shown in Table 3 and evaluated for its cleansing power and clean feeling. The skin cleansing composition was also evaluated for its fresh feeling after wiping, friction feeling after wiping, and absence of a sticky feeling after wiping by methods given below. The results are also shown in Table 3.

(Evaluation Method)
(1) Fresh Feeling after Wiping:

Ten female expert panelists applied each cleansing composition on a cosmetic cotton and wiped their made-up faces with the cotton. The panelists conducted sensory evaluation for a fresh feeling of the skin after wiping according to five grades: "5: Very fresh feeling", "4: Fresh feeling", "3: Slightly fresh feeling", "2: Not very fresh feeling" and "1: Not fresh feeling". The sum of the scores of the ten panelists was determined.

(2) Friction Feeling after Wiping:

Ten female expert panelists applied each cleansing composition on a cosmetic cotton and wiped their made-up faces with the cotton. The panelists conducted sensory evaluation for a feeling of friction of the skin after wiping according to five grades: "5: No feeling of friction", "4: Almost no feeling of friction", "3: Not much feeling of friction", "2: Slight feeling of friction" and "1: Strong feeling of friction". The sum of the scores of the ten panelists was determined.

(3) Absence of Sticky Feeling after Wiping:

Ten female expert panelists applied each cleansing composition on a cosmetic cotton and wiped their made-up faces with the cotton. The panelists conducted sensory evaluation for a sticky feeling of the skin after wiping according to five grades: "5: No sticky feeling", "4: Almost no sticky feeling", "3: Not much sticky feeling", "2: Slight sticky feeling" and "1: Strong sticky feeling". The sum of the scores of the ten panelists was determined.

TABLE 3

| | | Component (% by mass) | Example 9 | 13 | 14 | 15 | 16 | 17 | 18 | 19 |
|---|---|---|---|---|---|---|---|---|---|---|
| A | A-1 | (Acrylates/steareth-20 methacrylate) copolymer (manufactured by Rohm and Haas Company, ACULYN 22 (solid content: 30%)) | 1.50 | | | | | | 1.5 | 1.5 |
| | | (Acrylic acid/stearyl acrylate) copolymer (Synthesis Example 1) | | 0.45 | | | | | | |
| | | Polyquaternium-51 (manufactured by NOF Corp., Lipidure PMB, active ingredient: 5%) | | | 9.00 | | | | | |
| | | (Glycerylamidoethyl methacrylate/stearyl methacrylate) copolymer (manufactured by NOF Corp., Ceracute F) | | | | 0.45 | | | | |
| | A-2 | Hydroxyethyl(hydroxypropylpolyethylene glycol dodecyl ether)cellulose (Synthesis Example 2) | | | | | 0.45 | | | |
| | A-3 | Polyether polycarbonate (Synthesis Example 3) | | | | | | 0.45 | | |
| B | b1 | Dicaprylyl ether (manufactured by BASF Personal Care and Nutrition GmbH, Cetiol OE) | 6 | 6 | 6 | 6 | 6 | 6 | 20 | |
| | b2 | Isododecane (5 mPa · s) (manufactured by Maruzen Petrochemical Co., Ltd., MARUKASOL R) | | | | | | | | |
| | | Light liquid isoparaffin (5 mPa · s) (manufactured by NOF Corp., PARLEAM 4) | 14 | 14 | 14 | 14 | 14 | 14 | | 20 |
| | | Isohexadecane (5 mPa · s) (manufactured by LANXESS, Isohexadecane) | | | | | | | | |
| C | | Water | 73.17 | 74.22 | 65.67 | 74.22 | 74.36 | 74.22 | 73.17 | 73.17 |
| D | | Diglycerin monoisostearate (HLB: 8) (manufactured by The Nisshin Oillio Group, Ltd., COSMOL 41V) | | | | | | 0.005 | | |
| | | Polyoxyethylene sorbitan monostearate (HLB: 15) (manufactured by Kao Corp., RHEODOL TW-S120V) | 0.05 | 0.05 | 0.05 | 0.05 | 0.05 | 0.05 | 0.05 | 0.05 |
| E | | 1,3-Butylene glycol | 5 | 5 | 5 | 5 | 5 | 5 | 5 | 5 |
| | | Dipropylene glycol | | | | | | | | |
| | | PEG-400 | | | | | | | | |
| Others | | Sorbitan monostearate (HLB: 5) (manufactured by Kao Corp., RHEODOL SP-S10V) | 0.1 | 0.1 | 0.1 | 0.1 | 0.1 | 0.1 | 0.1 | 0.1 |
| | | Liquid paraffin (22.5 mPa · s) (manufactured by Kaneda Co., Ltd., HICALL K-230) | | | | | | | | |
| | | Fragrance | 0.03 | 0.03 | 0.03 | 0.03 | 0.03 | 0.03 | 0.03 | 0.03 |
| | | 48% KOH | 0.15 | 0.15 | 0.15 | 0.15 | 0.01 | 0.15 | 0.15 | 0.15 |
| | | Total | 100 | 100 | 100 | 100 | 100 | 100 | 100 | 100 |
| | | Active amount (%) of A | 0.45 | 0.45 | 0.45 | 0.45 | 0.45 | 0.45 | 0.45 | 0.45 |
| | | Total amount (%) of B | 20 | 20 | 20 | 20 | 20 | 20 | 20 | 20 |
| | | b1/A | 13.3 | 13.3 | 13.3 | 13.3 | 13.3 | 13.3 | 44.4 | 0.0 |
| | | b2/A | 31.1 | 31.1 | 31.1 | 31.1 | 31.1 | 31.1 | 0.0 | 44.4 |
| | | B/A | 44.4 | 44.4 | 44.4 | 44.4 | 44.4 | 44.4 | 44.4 | 44.4 |
| | | b1/b2 | 0.43 | 0.43 | 0.43 | 0.43 | 0.43 | 0.43 | — | 0 |
| | | Content (% by mass) of b2 in whole oil agents except for b1 | 100 | 100 | 100 | 100 | 100 | 100 | — | 100 |
| | | Cleansing power | 6 | 7 | 7 | 7 | 7 | 7 | 4 | 7 |
| | | Clean feeling | 41 | 40 | 40 | 40 | 41 | 41 | 39 | 41 |
| | | Fresh feeling after wiping | 42 | 42 | 42 | 42 | 42 | 42 | 42 | 42 |
| | | Feeling of friction after wiping | 43 | 43 | 43 | 43 | 43 | 43 | 43 | 29 |
| | | Absence of sticky feeling after wiping | 42 | 42 | 42 | 42 | 42 | 42 | 28 | 40 |

| | | Component (% by mass) | Example 20 | 21 | 22 | 23 | 24 | 25 | 26 | 27 |
|---|---|---|---|---|---|---|---|---|---|---|
| A | A-1 | (Acrylates/steareth-20 methacrylate) copolymer (manufactured by Rohm and Haas Company, ACULYN 22 (solid content: 30%)) | 2 | 0.35 | 1.5 | 1.5 | 1.5 | 1.5 | 1.5 | 1.5 |
| | | (Acrylic acid/stearyl acrylate) copolymer (Synthesis Example 1) | | | | | | | | |
| | | Polyquaternium-51 (manufactured by NOF Corp., Lipidure PMB, active ingredient: 5%) | | | | | | | | |
| | | (Glycerylamidoethyl methacrylate/stearyl methacrylate) copolymer (manufactured by NOF Corp., Ceracute F) | | | | | | | | |

TABLE 3-continued

|   |   |   | | | | | | | | |
|---|---|---|---|---|---|---|---|---|---|---|
| | A-2 | Hydroxyethyl(hydroxypropylpolyethylene glycol dodecyl ether)cellulose (Synthesis Example 2) | | | | | | | | |
| | A-3 | Polyether polycarbonate (Synthesis Example 3) | | | | | | | | |
| B | b1 | Dicaprylyl ether (manufactured by BASF Personal Care and Nutrition GmbH, Cetiol OE) | 1.5 | 6 | 15 | 6 | 6 | 6 | 6 | 6 |
| | b2 | Isododecane (5 mPa · s) (manufactured by Maruzen Petrochemical Co., Ltd., MARUKASOL R) | | | | | 7 | | | |
| | | Light liquid isoparaffin (5 mPa · s) (manufactured by NOF Corp., PARLEAM 4) | 3.5 | 14 | 5 | 6 | | 14 | 14 | 14 |
| | | Isohexadecane (5 mPa · s) (manufactured by LANXESS, Isohexadecane) | | | | | 7 | | | |
| C | | Water | 87.67 | 74.32 | 73.17 | 73.17 | 73.17 | 73.17 | 76.17 | 66.17 |
| D | | Diglycerin monoisostearate (HLB: 8) (manufactured by The Nisshin Oillio Group, Ltd., COSMOL 41V) | | | | | | | | |
| | | Polyoxyethylene sorbitan monostearate (HLB: 15) (manufactured by Kao Corp., RHEODOL TW-S120V) | 0.05 | 0.05 | 0.05 | 0.05 | 0.05 | 0.05 | 0.05 | 0.05 |
| E | | 1,3-Butylene glycol | 5 | 5 | 5 | 5 | 5 | | 2 | 12 |
| | | Dipropylene glycol | | | | | | 2 | | |
| | | PEG-400 | | | | | | 3 | | |
| Others | | Sorbitan monostearate (HLB: 5) (manufactured by Kao Corp., RHEODOL SP-S10V) | 0.1 | 0.1 | 0.1 | 0.1 | 0.1 | 0.1 | 0.1 | 0.1 |
| | | Liquid paraffin (22.5 mPa · s) (manufactured by Kaneda Co., Ltd., HICALL K-230) | | | | 8 | | | | |
| | | Fragrance | 0.03 | 0.03 | 0.03 | 0.03 | 0.03 | 0.03 | 0.03 | 0.03 |
| | | 48% KOH | 0.15 | 0.15 | 0.15 | 0.15 | 0.15 | 0.15 | 0.15 | 0.15 |
| | | Total | 100 | 100 | 100 | 100 | 100 | 100 | 100 | 100 |
| | | Active amount (%) of A | 0.60 | 0.11 | 0.45 | 0.45 | 0.45 | 0.45 | 0.45 | 0.45 |
| | | Total amount (%) of B | 5 | 20 | 20 | 12 | 20 | 20 | 20 | 20 |
| | | b1/A | 2.5 | 57.1 | 33.3 | 13.3 | 13.3 | 13.3 | 13.3 | 13.3 |
| | | b2/A | 5.8 | 133.3 | 11.1 | 13.3 | 31.1 | 31.1 | 31.1 | 31.1 |
| | | B/A | 8.3 | 190.5 | 44.4 | 26.7 | 44.4 | 44.4 | 44.4 | 44.4 |
| | | b1/b2 | 0.43 | 0.43 | 3 | 1 | 0.43 | 0.43 | 0.43 | 0.43 |
| | | Content (% by mass) of b2 in whole oil agents except for b1 | 100 | 100 | 100 | 42.9 | 100 | 100 | 100 | 100 |
| | | Cleansing power | 12 | 5 | 5 | 15 | 6 | 6 | 6 | 6 |
| | | Clean feeling | 42 | 37 | 40 | 40 | 41 | 41 | 41 | 39 |
| | | Fresh feeling after wiping | 42 | 42 | 42 | 42 | 42 | 42 | 42 | 40 |
| | | Feeling of friction after wiping | 43 | 43 | 43 | 43 | 43 | 43 | 43 | 41 |
| | | Absence of sticky feeling after wiping | 42 | 42 | 42 | 42 | 42 | 42 | 42 | 40 |

Examples 28 and 29 and Comparative Examples 6 to 8

Each skin cleansing composition was prepared according to the composition shown in Table 4 and evaluated for its residual oil agent level after wiping, film shape, cleansing power for oil-based mascara, clean feeling of the skin after wiping, duration of a smooth feel of the skin after wiping, and duration of softness of the skin after wiping. The results are also shown in Table 4.

(Production Method)

The component (H) was added to water at 60° C. and uniformly stirred. Then, the component (G) was added to the mixture and stirred for uniform mixing. Then, a hydrocarbon oil as the component (I) was added to the mixture with stirring and dispersed therein, and 48% potassium hydroxide was further added thereto to give a skin cleansing composition.

(Evaluation Method)

(1) Residual Oil Agent Level after Wiping:

A region of forearm was washed with a detergent for dishwashing (manufactured by Kao Corp., Kyukyutto), and moisture was wiped off with a paper towel, followed by drying at room temperature for 10 minutes. Approximately 2 g of each skin cleansing composition was uniformly applied on a commercially available cosmetic cotton. The region of forearm was wiped using the cosmetic cotton. Within 10 seconds, the region of forearm was loaded in a measurement apparatus where a residual oil agent level (peak area ratio of spectra: which was evaluated from the difference between the measurement value of the arm thus washed with the detergent for dishwashing and the measurement value after this test) was then determined on the basis of infrared absorption spectra. The measurement apparatus used was a Fourier transform infrared spectrophotometer (manufactured by Thermo Scientific Inc.).

(2) Film Shape:

0.1 g of each obtained skin cleansing composition was added dropwise onto a glass plate within 5 seconds immediately after preparation and was allowed to stand at room temperature for 1 day for drying. The obtained film-like substance was evaluated for its texture against the skin (smooth feel). The evaluation was carried out by touching with the fingers of five expert panelists and indicated by the sum of the scores of the five panelists.

5: Very smooth
4: Smooth.
3: Slightly smooth.
2: Not so much smooth.
1: Not smooth.

(3) Cleansing Power for Oil-Based Mascara:

0.005 g of KOSE Sports Beauty Fasio Power Stay Mascara (Curl Long) BK001 (trade name) was uniformly applied as oil-based mascara (waterproof mascara) in a circular pattern of 1.2 cm in diameter onto slide glass and allowed to stand for 2 hours for drying. Approximately 0.05 g of each skin cleansing composition was put on the oil-based mascara and massaged in a circular motion with fingers for 10 seconds. The oil-based mascara was wiped off by force at a given pressure (7.8 kPa) using a cotton. Mascara residues on the slide glass were visually evaluated according to five grades given below. The evaluation was indicated by the sum of the scores of five expert panelists.
5: No mascara remains.
4: Approximately 5% or less of the mascara remains.
3: Approximately 5 to approximately 10% of the mascara remains.
2: Approximately 10 to approximately 50% of the mascara remains.
1: More than approximately 50% of the mascara remains.
(4) Clean Feeling of Skin after Wiping:

Five expert panelists uniformly applied 4 g of each skin cleansing composition on a cosmetic cotton (LILY BELL Lilian Puff/Suzuran Sanitary Goods Co., Ltd.; the same cosmetic cotton was used in subsequent evaluations) and then wiped their foundation (Sofina Primavista Liquid Foundation Ocher 05; the same foundation was used in subsequent evaluations)—applied faces using the cotton. The panelists conducted sensory evaluation for a clean feeling of the skin after 15 seconds immediately after the wiping according to five levels given below. The total of the scores of the five panelists was determined.
5: Very good.
4: Good.
3: Slightly good.
2: Not very good.
1: Not good.
(5) Duration of Smooth Feel of the Skin after Wiping:

Five expert panelists uniformly applied 4 g of each skin cleansing composition on a cosmetic cotton and then wiped their foundation-applied faces using the cotton.

The panelists kept quiet for 3 hours in a room of 30° C. and 60% RH and then conducted sensory evaluation for a smooth feel of the skin according to five grades given below. The sum of the scores of the five panelists was determined.
5: Very smooth feel lasts very long.
4: Smooth feel lasts long.
3: Slightly smooth feel lasts.
2: Smooth feel does not last so much.
1: Smooth feel does not last.
(6) Duration of Softness of Skin after Wiping:

Five expert panelists uniformly applied 4 g of each cleansing composition on a cosmetic cotton and then wiped their foundation-applied faces with the cotton. The panelists kept quiet for 3 hours in a room of 30° C. and 60% RH and then conducted sensory evaluation for softness of the skin according to five grades given below. The sum of the scores of the five panelists was determined.
5: Very soft.
4: Soft.
3: Slightly soft.
2: Not so soft.
1: Not Soft.

TABLE 4

| | Component (% by mass) | Example 28 | Example 29 | Comparative Example 6 | Comparative Example 7 | Comparative Example 8 |
|---|---|---|---|---|---|---|
| G | (Acrylates/steareth-20 methacrylate) copolymer (manufactured by Rohm and Haas Company, ACULYN 22 (solid content: 30%)) | 1.67 | 1.67 | 1.67 | | 1.67 |
| H | Acrylic acid/alkyl (C10-30) methacrylate copolymer (manufactured by Lubrizol Advanced Materials, PEMULEN TR-2) | 0.1 | | | | |
| | Carboxyvinyl polymer (manufactured by Lubrizol Advanced Materials, Carbopol 980) | | 0.1 | | 0.1 | 0.1 |
| I | Light liquid isoparaffin (5 mPa·s) (manufactured by NOF Corp., PARLEAM 4) | 10 | 10 | 10 | 10 | 0.1 |
| J | Purified water | 88.01 | 88.01 | 88.16 | 89.85 | 98.08 |
| | 48% KOH | 0.22 | 0.22 | 0.17 | 0.05 | 0.05 |
| | Total | 100 | 100 | 100 | 100 | 100 |
| | Active amount (%) of G | 0.5 | 0.5 | 0.5 | 0.0 | 0.5 |
| | (G)/(H) | 5.0 | 5.0 | — | 0.0 | 5.0 |
| | (G)/(Total amount of oil agents) | 0.1 | 0.1 | 0.1 | 0.0 | 5.0 |
| | Residual oil agent level after wiping | 160 | 170 | 320 | 817 | 8 |
| | Film shape | 25 | 25 | 9 | 9 | 13 |
| | Cleansing power for oil-based mascara | 25 | 25 | 25 | 25 | 1 |
| | Clean feeling of skin after wiping | 25 | 25 | 23 | 8 | 23 |
| | Duration of smooth feel of skin after wiping | 25 | 25 | 7 | 5 | 13 |
| | Duration of softness of skin after wiping | 25 | 25 | 6 | 4 | 12 |

Examples 30 to 38

Each skin cleansing composition was prepared according to the formulation shown in Table 5 and evaluated for its cleansing power for oil-based mascara, clean feeling of the skin after wiping, duration of a smooth feel of the skin after wiping, and duration of softness of the skin after wiping in the same way as in Examples 28 and 29. The results are also shown in Table 5.

(Preparation Method)

The components (I), (K), (L), and (M) and oil agents were mixed and the mixture was stirred at 60° C. to prepare an oil phase. Methylparaben was added to water at 60° C. and dissolved therein. The component (H) was further added thereto and the mixture was uniformly stirred. The components (G) and (N) and phenoxyethanol were added thereto to prepare an aqueous phase. Then, the oil phase was added to the aqueous phase and the mixture was stirred. The mixture was then neutralized with 48% KOH and the mixture was cooled to room temperature. The other components were added thereto and the mixture was further stirred to give a cleansing composition.

TABLE 5

| Component (% by mass) | | Example 30 | Example 31 | Example 32 | Example 33 | Example 34 |
|---|---|---|---|---|---|---|
| G | (Acrylates/steareth-20 methacrylate) copolymer (manufactured by Rohm and Haas Company, ACULYN 22 (solid content: 30%)) | 1.67 | 0.67 | 8.00 | 1.67 | 1.67 |
| H | Carboxyvinyl polymer (manufactured by Lubrizol Advanced Materials, Carbopol 980) | 0.03 | 0.03 | 0.03 | 0.01 | 0.60 |
| I | Light liquid isoparaffin (5 mPa · s) (manufactured by NOF Corp., PARLEAM 4) | 4.40 | 4.40 | 4.40 | 4.40 | 4.40 |
|   | Isododecane (5 mPa · s) (manufactured by Maruzen Petrochemical Co., Ltd., MARUKASOL R) | 4.40 | 4.40 | 4.40 | 4.40 | 4.40 |
| L | Dioctyl ether (manufactured by BASF Personal Care and Nutrition GmbH, Cetiol OE) | 6.00 | 6.00 | 6.00 | 6.00 | 6.00 |
| M | Dimethylpolysiloxane (manufactured by Shin-Etsu Chemical Co., Ltd., Silicone KF-96L-2CS) | 3.20 | 3.20 | 3.20 | 3.20 | 3.20 |
| K | Polyoxyethylene hydrogenated castor oil (HLB: 14) (manufactured by Kao Corp., EMANON CH-60(K)) | 0.08 | 0.08 | 0.08 | 0.08 | 0.08 |
|   | Sorbitan monostearate (HLB: 4.7) (manufactured by Kao Corp., RHEODOL SP-S10V) | 0.08 | 0.08 | 0.08 | 0.08 | 0.08 |
| N | Dipropylene glycol | 3.00 | 3.00 | 3.00 | 3.00 | 3.00 |
|   | 1,3-Butylene glycol | 2.00 | 2.00 | 2.00 | 2.00 | 2.00 |
|   | Isopropyl myristate (5 mPa · s) (manufactured by Kao Corp., EXCEPARL IPM) | 3.20 | 3.20 | 3.20 | 3.20 | 3.20 |
|   | Sodium hyaluronate (2) | 0.0001 | 0.0001 | 0.0001 | 0.0001 | 0.0001 |
|   | Liquid potassium hydroxide (48%) | 0.18 | 0.10 | 0.84 | 0.18 | 0.18 |
|   | Phenoxyethanol | 0.40 | 0.40 | 0.40 | 0.40 | 0.40 |
|   | Methyl parahydroxybenzoate | 0.10 | 0.10 | 0.10 | 0.10 | 0.10 |
|   | Water-soluble collagen solution | 0.001 | 0.001 | 0.001 | 0.001 | 0.001 |
|   | Fragrance | 0.03 | 0.03 | 0.03 | 0.03 | 0.03 |
| J | Purified water | 71.24 | 72.32 | 64.25 | 71.26 | 70.67 |
|   | Total | 100.00 | 100.00 | 100.00 | 100.00 | 100.00 |
|   | Active amount (%) of G | 0.50 | 0.20 | 2.40 | 0.50 | 0.50 |
|   | G/H | 16.70 | 6.70 | 80.00 | 50.10 | 0.84 |
|   | G/Total amount of oil agents | 0.02 | 0.01 | 0.11 | 0.02 | 0.02 |
|   | (G + H)/Total amount of oil agents | 0.03 | 0.01 | 0.11 | 0.02 | 0.05 |
|   | I + L + M | 18.00 | 18.00 | 18.00 | 18.00 | 18.00 |
|   | Cleansing power for oil-based mascara | 25 | 25 | 19 | 25 | 21 |
|   | Clean feeling of skin after wiping | 25 | 18 | 25 | 25 | 25 |
|   | Duration of smooth feel of skin after wiping | 25 | 21 | 25 | 21 | 25 |
|   | Duration of softness of skin after wiping | 25 | 21 | 25 | 21 | 25 |

| Component (% by mass) | | Example 35 | Example 36 | Example 37 | Example 38 |
|---|---|---|---|---|---|
| G | (Acrylates/steareth-20 methacrylate) copolymer (manufactured by Rohm and Haas Company, ACULYN 22 (solid content: 30%)) | 1.67 | 1.67 | 0.67 | 8.00 |
| H | Carboxyvinyl polymer (manufactured by Lubrizol Advanced Materials, Carbopol 980) | 0.03 | 0.03 | 0.60 | 0.02 |
| I | Light liquid isoparaffin (5 mPa · s) (manufactured by NOF Corp., PARLEAM 4) | 1.00 | 8.80 | 4.40 | 0.50 |
|   | Isododecane (5 mPa · s) (manufactured by Maruzen Petrochemical Co., Ltd., MARUKASOL R) | 1.00 | 8.80 | 4.40 | 0.50 |
| L | Dioctyl ether (manufactured by BASF Personal Care and Nutrition GmbH, Cetiol OE) | 6.00 | 6.00 | 6.00 | 6.00 |
| M | Dimethylpolysiloxane (manufactured by Shin-Etsu Chemical Co., Ltd., Silicone KF-96L-2CS) | 3.20 | 3.20 | 3.20 | 3.20 |
| K | Polyoxyethylene hydrogenated castor oil (HLB: 14) (manufactured by Kao Corp., EMANON CH-60(K)) | 0.08 | 0.08 | 0.08 | 0.08 |
|   | Sorbitan monostearate (HLB: 4.7) (manufactured by Kao Corp., RHEODOL SP-S10V) | 0.08 | 0.08 | 0.08 | 0.08 |
| N | Dipropylene glycol | 3.00 | 3.00 | 3.00 | 3.00 |
|   | 1,3-Butylene glycol | 2.00 | 2.00 | 2.00 | 2.00 |
|   | Isopropyl myristate (5 mPa · s) (manufactured by Kao Corp., EXCEPARL IPM) | 3.20 | 3.20 | 3.20 | 3.20 |
|   | Sodium hyaluronate (2) | 0.0001 | 0.0001 | 0.0001 | 0.0001 |
|   | Liquid potassium hydroxide (48%) | 0.18 | 0.18 | 0.67 | 0.83 |
|   | Phenoxyethanol | 0.40 | 0.40 | 0.40 | 0.40 |
|   | Methyl parahydroxybenzoate | 0.10 | 0.10 | 0.10 | 0.10 |
|   | Water-soluble collagen solution | 0.001 | 0.001 | 0.001 | 0.001 |
|   | Fragrance | 0.03 | 0.03 | 0.03 | 0.03 |
| J | Purified water | 78.04 | 62.44 | 71.18 | 72.07 |
|   | Total | 100.00 | 100.00 | 100.00 | 100.00 |
|   | Active amount (%) of G | 0.50 | 0.50 | 0.20 | 2.40 |
|   | G/H | 16.70 | 16.70 | 0.34 | 120.00 |
|   | G/Total amount of oil agents | 0.03 | 0.02 | 0.01 | 0.18 |
|   | (G + H)/Total amount of oil agents | 0.04 | 0.02 | 0.04 | 0.18 |
|   | I + L + M | 11.20 | 26.80 | 18.00 | 10.20 |
|   | Cleansing power for oil-based mascara | 17 | 25 | 25 | 16 |
|   | Clean feeling of skin after wiping | 23 | 19 | 16 | 23 |
|   | Duration of smooth feel of skin after wiping | 24 | 20 | 15 | 22 |
|   | Duration of softness of skin after wiping | 24 | 19 | 15 | 22 |

Example 39

A skin cleansing composition (cleansing sheet) was prepared according to the formula shown in Table 6. The composition was evaluated for its cleansing power for oil-based mascara, clean feeling of the skin after wiping, duration of a smooth feel of the skin after wiping, and duration of softness of the skin after wiping in the same way as in Examples 28 and 29. The results are also shown in Table 6.

(Preparation Method)

Methylparaben was dissolved in water at 60° C. The component (H) is further added to the solution and uniformly stirred, followed by neutralization with 48% KOH. The component (N) was further added to the mixture and stirred to give an aqueous phase. The components (G), (I), (K), and (M) were mixed at 60° C. to give an oil phase. Then, the oil phase was added to the aqueous phase and stirred, followed by cooling to 50° C. The component (L) was added thereto and stirred, followed by cooling to room temperature. Then, the other components were further added thereto and stirred to give a cleansing composition. Non-woven cloth was impregnated with this cleansing composition to give a cleansing sheet.

TABLE 6

| | Component (% by mass) | Example 39 |
|---|---|---|
| G | (Acrylates/steareth-20 methacrylate) copolymer (manufactured by Rohm and Haas Company, ACULYN 22 (solid content: 30%)) | 0.67 |
| H | Carboxyvinyl polymer (manufactured by Lubrizol Advanced Materials, Carbopol 980) | 0.03 |
| I | Isododecane (5 mPa · s) (manufactured by Maruzen Petrochemical Co., Ltd., MARUKASOL R) | 7.00 |
| L | Dioctyl ether (manufactured by BASF Personal Care and Nutrition GmbH, Cetiol OE) | 7.00 |
| M | Dimethylpolysiloxane (manufactured by Shin-Etsu Chemical Co., Ltd., Silicone KF-96L-2CS) | 2.00 |
| K | Polyoxyethylene hydrogenated castor oil (HLB: 14) (manufactured by Kao Corp., EMANON CH-60(K)) | 0.05 |
| N | 1,3-Butylene glycol | 5.00 |
| | PPG-9 diglyceryl (manufactured by Sakamoto Yakuhin Kogyo Co., Ltd., SY-DP9) | 4.00 |

TABLE 6-continued

| | Component (% by mass) | Example 39 |
|---|---|---|
| | Fragrance | 0.03 |
| | 48% KOH | 0.10 |
| | Methylparaben | 0.10 |
| | Phenoxyethanol | 0.30 |
| J | Purified water | 73.72 |
| | Total | 100.00 |
| | Active amount (%) of G | 0.20 |
| | G/H | 6.70 |
| | G/Total amount of oil agents | 0.01 |
| | (G + H)/Total amount of oil agents | 0.01 |
| | I + L + M | 16.00 |
| | Cleansing power for oil-based mascara | 25 |
| | Clean feeling of skin after wiping | 25 |
| | Duration of smooth feel of skin after wiping | 25 |
| | Duration of softness of skin after wiping | 25 |

Examples 40 to 47 and Comparative Example 9

In the same way as in Examples 30 to 38, each skin cleansing composition was prepared according to the composition shown in Table 7 and evaluated for its cleansing power for oil-based mascara, clean feeling of the skin after wiping, duration of a smooth feel of the skin after wiping, and duration of softness of the skin after wiping. The skin cleansing composition was also evaluated for its fresh feeling of the skin after wiping by a method given below. The results are also shown in Table 7.

(Evaluation Method)

Five expert panelists uniformly applied 4 g of each skin cleansing composition on a cosmetic cotton and then wiped their foundation-applied faces with the cotton.

The panelists conducted sensory evaluation for a fresh feeling of the skin immediately thereafter according to five grades given below. The sum of the scores of the five panelists was determined.

5: Felt very fresh.
4: Felt fresh.
3: Felt slightly fresh.
2: Felt not so fresh.
1: Felt no fresh.

TABLE 7

| | | Component (% by mass) | Example 30 | Example 40 | Example 41 | Example 42 | Example 43 |
|---|---|---|---|---|---|---|---|
| G | G-1 | (Acrylates/steareth-20 methacrylate) copolymer (manufactured by Rohm and Haas Company, ACULYN 22 (solid content: 30%)) | 1.67 | | | | |
| | | (Acrylic acid/stearyl acrylate) copolymer (Synthesis Example 1) | | 0.50 | | | |
| | | Polyquaternium-51 (manufactured by NOF Corp., Lipidure PMB, active ingredient: 5%) | | | 10.00 | | |
| | | (Glycerylamidoethyl methacrylate/stearyl methacrylate) copolymer (manufactured by NOF Corp., Ceracute F) | | | | 0.50 | |
| | G-2 | Hydroxyethyl(hydroxypropylpolyethylene glycol dodecyl ether)cellulose (Synthesis Example 2) | | | | | 0.50 |
| | G-3 | Polyether polycarbonate (Synthesis Example 3) | | | | | |
| H | | Carboxyvinyl polymer (manufactured by Lubrizol Advanced Materials, Carbopol 980) | 0.03 | 0.03 | 0.03 | 0.03 | 0.03 |
| I | | Light liquid isoparaffin (5 mPa · s) (manufactured by NOF Corp., PARLEAM 4) | 4.40 | 4.40 | 4.40 | 4.40 | 4.40 |
| | | Isododecane (5 mPa · s) (manufactured by Maruzen Petrochemical Co., Ltd., MARUKASOL R) | 4.40 | 4.40 | 4.40 | 4.40 | 4.40 |
| | | Liquid paraffin (22.5 mPa · s) (manufactured by Kaneda Co., Ltd., HICALL K-230) | | | | | |
| L | | Dicaprylyl ether (manufactured by BASF Personal Care and Nutrition GmbH, Cetiol OE) | 6.00 | 6.00 | 6.00 | 6.00 | 6.00 |
| M | | Dimethicone (manufactured by Shin-Etsu Chemical Co., Ltd., KF-96-2cs) | 3.20 | 3.20 | 3.20 | 3.20 | 3.20 |

TABLE 7-continued

| | | Component (% by mass) | | | | | |
|---|---|---|---|---|---|---|---|
| K | | Polyoxyethylene hydrogenated castor oil (HLB: 14) (manufactured by Kao Corp., EMANON CH-60) | 0.08 | 0.08 | 0.08 | 0.08 | 0.08 |
| | | Sorbitan monostearate (HLB: 5) (manufactured by Kao Corp., RHEODOL SP-S10V) | 0.08 | 0.08 | 0.08 | 0.08 | 0.08 |
| N | | Dipropylene glycol | 3.00 | 3.00 | 3.00 | 3.00 | 3.00 |
| | | 1,3-Butylene glycol | 2.00 | 2.00 | 2.00 | 2.00 | 2.00 |
| | | Isopropyl myristate | 3.20 | 3.20 | 3.20 | 3.20 | 3.20 |
| | | Sodium hyaluronate | 0.0001 | 0.0001 | 0.0001 | 0.0001 | 0.0001 |
| | | Liquid potassium hydroxide (48%) | 0.18 | 0.18 | 0.18 | 0.18 | 0.18 |
| | | Phenoxyethanol | 0.40 | 0.40 | 0.40 | 0.40 | 0.40 |
| | | Methyl parahydroxybenzoate | 0.10 | 0.10 | 0.10 | 0.10 | 0.10 |
| | | Water-soluble collagen | 0.001 | 0.001 | 0.001 | 0.001 | 0.001 |
| | | Fragrance | 0.03 | 0.03 | 0.03 | 0.03 | 0.03 |
| J | | Purified water | 71.23 | 72.40 | 62.90 | 72.40 | 72.40 |
| | | Total | 100.00 | 100.00 | 100.00 | 100.00 | 100.00 |
| | | Active amount (%) of G | 0.50 | 0.50 | 0.50 | 0.50 | 0.50 |
| | | G/H | 16.70 | 16.67 | 16.67 | 16.67 | 16.67 |
| | | G/Total amount of oil agents | 0.02 | 0.02 | 0.02 | 0.02 | 0.02 |
| | | (G + H)/Total amount of oil agents | 0.03 | 0.02 | 0.02 | 0.02 | 0.02 |
| | | I + L + M | 18.00 | 18.00 | 18.00 | 18.00 | 18.00 |
| | | Cleansing power for oil-based mascara | 25 | 25 | 25 | 25 | 25 |
| | | Clean feeling of skin after wiping | 25 | 24 | 24 | 24 | 24 |
| | | Duration of smooth feel of skin after wiping | 25 | 25 | 25 | 25 | 25 |
| | | Duration of softness of skin after wiping | 25 | 25 | 25 | 25 | 25 |
| | | Fresh feeling after wiping | 25 | 24 | 24 | 24 | 24 |

| | | | Example | | | | Comparative Example |
|---|---|---|---|---|---|---|---|
| | | Component (% by mass) | 44 | 45 | 46 | 47 | 9 |
| G | G-1 | (Acrylates/stereth-20 methacrylate) copolymer (manufactured by Rohm and Haas Company, ACULYN 22 (solid content: 30%)) | | 1.67 | 1.67 | 1.67 | 1.67 |
| | | (Acrylic acid/stearyl acrylate) copolymer (Synthesis Example 1) | | | | | |
| | | Polyquaternium-51 (manufactured by NOF Corp., Lipidure PMB, active ingredient: 5%) | | | | | |
| | | (Glycerylamidoethyl methacrylate/stearyl methacrylate) copolymer (manufactured by NOF Corp., Ceracute F) | | | | | |
| | G-2 | Hydroxyethyl(hydroxypropylpolyethylene glycol dodecyl ether)cellulose (Synthesis Example 2) | | | | | |
| | G-3 | Polyether polycarbonate (Synthesis Example 3) | 0.50 | | | | |
| H | | Carboxyvinyl polymer (manufactured by Lubrizol Advanced Materials, Carbopol 980) | 0.03 | 0.03 | 0.03 | 0.03 | 0.03 |
| I | | Light liquid isoparaffin (5 mPa · s) (manufactured by NOF Corp., PARLEAM 4) | 4.40 | 1.10 | 4.40 | 4.40 | |
| | | Isododecane (5 mPa · s) (manufactured by Maruzen Petrochemical Co., Ltd., MARUKASOL R) | 4.40 | 1.10 | 4.40 | 4.40 | |
| | | Liquid paraffin (22.5 mPa · s) (manufactured by Kaneda Co., Ltd., HICALL K-230) | | | | | 8.80 |
| L | | Dicaprylyl ether (manufactured by BASF Personal Care and Nutrition GmbH, Cetiol OE) | 6.00 | 1.50 | 10.00 | 6.00 | 6.00 |
| M | | Dimethicone (manufactured by Shin-Etsu Chemical Co., Ltd., KF-96-2cs) | 3.20 | 0.80 | 3.20 | 6.00 | 3.20 |
| K | | Polyoxyethylene hydrogenated castor oil (HLB: 14) (manufactured by Kao Corp., EMANON CH-60) | 0.08 | 0.08 | 0.08 | 0.08 | 0.08 |
| | | Sorbitan monostearate (HLB: 5) (manufactured by Kao Corp., RHEODOL SP-S10V) | 0.08 | 0.08 | 0.08 | 0.08 | 0.08 |
| N | | Dipropylene glycol | 3.00 | 3.00 | 3.00 | 3.00 | 3.00 |
| | | 1,3-Butylene glycol | 2.00 | 2.00 | 2.00 | 2.00 | 2.00 |
| | | Isopropyl myristate | 3.20 | 3.20 | 3.20 | 3.20 | 3.20 |
| | | Sodium hyaluronate | 0.0001 | 0.0001 | 0.0001 | 0.0001 | 0.0001 |
| | | Liquid potassium hydroxide (48%) | 0.18 | 0.18 | 0.18 | 0.18 | 0.18 |
| | | Phenoxyethanol | 0.40 | 0.40 | 0.40 | 0.40 | 0.40 |
| | | Methyl parahydroxybenzoate | 0.10 | 0.10 | 0.10 | 0.10 | 0.10 |
| | | Water-soluble collagen | 0.001 | 0.001 | 0.001 | 0.001 | 0.001 |
| | | Fragrance | 0.03 | 0.03 | 0.03 | 0.03 | 0.03 |
| J | | Purified water | 72.40 | 84.73 | 67.23 | 68.43 | 71.23 |
| | | Total | 100.00 | 100.00 | 100.00 | 100.00 | 100.00 |
| | | Active amount (%) of G | 0.05 | 0.50 | 0.50 | 0.50 | 0.50 |
| | | G/H | 1.67 | 16.70 | 16.70 | 16.70 | 16.70 |
| | | G/Total amount of oil agents | 0.00 | 0.06 | 0.02 | 0.02 | 0.02 |
| | | (G + H)/Total amount of oil agents | 0.00 | 0.07 | 0.02 | 0.02 | 0.03 |
| | | I + L + M | 18.00 | 4.50 | 22.00 | 20.80 | 9.20 |
| | | Cleansing power for oil-based mascara | 25 | 20 | 25 | 25 | 14 |
| | | Clean feeling of skin after wiping | 24 | 25 | 25 | 25 | 18 |
| | | Duration of smooth feel of skin after wiping | 25 | 25 | 25 | 25 | 21 |
| | | Duration of softness of skin after wiping | 25 | 25 | 25 | 25 | 21 |
| | | Fresh feeling after wiping | 25 | 25 | 25 | 25 | 22 |

The invention claimed is:
1. A cleansing composition comprising components (A), (B), and (C):
   (A) 0.001 to 5% by mass of a polymer selected from the group consisting of (A-1), (A-2), and (A-3):
   (A-1) a copolymer comprising monomers selected from the group consisting of (a1), (a2), and (a3) as constitutional units:
      (a1) a monomer selected from the group consisting of acrylic acid and methacrylic acid,
      (a2) a monomer selected from the group consisting of an acrylic acid alkyl ester and a methacrylic acid alkyl ester, and
      (a3) a monomer selected from the group consisting of a polyoxyethylene alkyl ester of acrylic acid and a polyoxyethylene alkyl ester of methacrylic acid,
      and comprising 10 mol % or more of (a2) as represented by mol % based on the total monomers;
   (A-2) a polysaccharide derivative having a polyoxyalkylene chain having an average molecular weight of 300 to 100,000 and having a constitutional unit represented by formula (1):

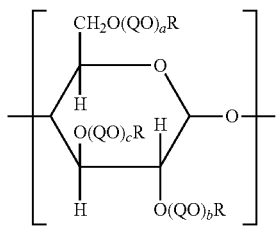

wherein R identically or differently represents a group selected from the group consisting of (d) a hydrogen atom, a methyl group, an ethyl group, a hydroxyethyl group, and a hydroxypropyl group, (e) a substituent comprising a polyoxyalkylene group, (f) a sulfoalkyl group, (g) a carboxyalkyl group, and (h) a cationic substituent; Q identically or differently represents an alkylene group having 2 to 4 carbon atoms; a, b, and c identically or differently represent a number of 0 to 10; the QO groups, the R groups, or the numbers a, b, and c are identical or different in each repeating unit or between repeating units; and when each of the substituents (e) to (h) has a hydroxy group, the hydroxy group is optionally further substituted by any of other substituents (e) to (h), provided that at least one or more substituents (e) exist as R; and
   (A-3) a polyether polycarbonate having a constitutional unit represented by formula (2):

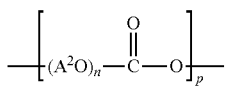

wherein $A^2$ represents an alkylene group having 2 to 6 carbon atoms; n represents a number of 5 to 1,000 on average; p represents a number of 5 to 100 on average; and $A^2$, having a number of (n×p) units, are identical or different;

(B) 1 to 50% by mass of an oil agent comprising (b1) and (b2):
      (b1) an ether oil and
      (b2) a hydrocarbon oil having a viscosity of 18 mPas or lower at 30° C.; and
   (C) water, and
comprising
   (D) no nonionic surfactant having HLB of 8 or more or less than 5% by mass of the nonionic surfactant,
   wherein the mass ratio of the total content of a fat in a paste or wax state at 30° C. to the content of said component (A) is 1/10 or less,
   wherein said water is present in an amount of at least 65% by mass.

2. The cleansing composition according to claim 1, wherein the component (A) is (A-1) which is a copolymer comprising (a1), (a2), and (a3) as constitutional units:
   (a1) a monomer selected from the group consisting of acrylic acid and methacrylic acid,
   (a2) a monomer selected from the group consisting of an acrylic acid alkyl ester and a methacrylic acid alkyl ester, and
   (a3) a monomer selected from the group consisting of a polyoxyethylene alkyl ester of acrylic acid and a polyoxyethylene alkyl ester of methacrylic acid
   and comprising 10 mol % or more of (a2) as represented by mol % based on the total monomers.

3. The cleansing composition according to claim 2, wherein the component (A) is a copolymer comprising as constitutional units:
   (a1) a monomer selected from the group consisting of acrylic acid and methacrylic acid,
   (a2) a monomer selected from the group consisting of an acrylic acid alkyl ester and a methacrylic acid alkyl ester, wherein the alkyl ester has 1 to 22 carbon atoms, and
   (a3) a monomer selected from the group consisting of a polyoxyethylene alkyl ester of acrylic acid and a polyoxyethylene alkyl ester of methacrylic acid, wherein the addition molar number of polyoxyethylene is 10 to 30, and the alkyl group has 12 to 22 carbon atoms,
   and comprising 10 mol % or more of (a2) as represented by mol % based on the total monomers.

4. The cleansing composition according to claim 2, wherein the component (A) is a copolymer comprising as constitutional units:
   (a1) at least one monomer selected from the group consisting of acrylic acid and methacrylic acid,
   (a2) a monomer selected from the group consisting of an acrylic acid alkyl ester and a methacrylic acid alkyl ester, wherein the alkyl ester has 1 to 22 carbon atoms, and
   (a3) a monomer selected from the group consisting of ester of acrylic acid and polyoxyethylene (20) stearyl ether, ester of methacrylic acid and polyoxyethylene (20) stearyl ether, ester of acrylic acid and polyoxyethylene (25) behenyl ether, and ester of methacrylic acid and polyoxyethylene (25) behenyl ether,
   and comprising 10 mol % or more of (a2) as represented by mol % based on the total monomers.

5. The cleansing composition according to claim 2, wherein the component (A) is selected from the group consisting of
   an (acrylate/steareth-20 methacrylate) copolymer, an (acrylate/steareth-20 methacrylate) crosspolymer, and an (acrylate/beheneth-25 methacrylate) copolymer.

6. The cleansing composition according to claim 1, wherein the mass ratio of the component (B) to the component (A), (B)/(A) is 0.5 to 400.

7. The cleansing composition according to claim 1, wherein the mass ratio of the component (b1) to the component (b2), (b1)/(b2) is 0.05 to 30.

8. The cleansing composition according to claim 1, wherein the content of the component (b2) is an amount exceeding 35% by mass in whole oil agents except for the component (b1).

9. The cleansing composition according to claim 1, further comprising (E) 15% by mass or less of a polyol.

10. The cleansing composition according to claim 1, further comprising (F) 15% by mass or less of ethanol.

11. A cleansing composition comprising components (A), (B), and (C):
(A) 0.001 to 5% by mass of a polymer selected from the group consisting of (A-1), (A-2), and (A-3):
(A-1) a copolymer comprising monomers selected from the group consisting of (a1), (a2), and (a3) as constitutional units:
(a1) a monomer selected from the group consisting of acrylic acid and methacrylic acid,
(a2) a monomer selected from the group consisting of an acrylic acid alkyl ester and a methacrylic acid alkyl ester, and
(a3) a monomer selected from the group consisting of a polyoxyethylene alkyl ester of acrylic acid and a polyoxyethylene alkyl ester of methacrylic acid,
and comprising 10 mol % or more of (a2) as represented by mol % based on the total monomers;
(A-2) a polysaccharide derivative having a polyoxyalkylene chain having an average molecular weight of 300 to 100,000 and having a constitutional unit represented by formula (1):

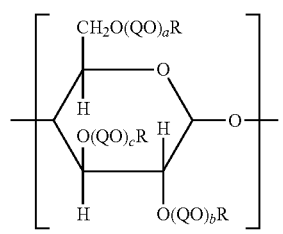

wherein R identically or differently represents a group selected from the group consisting of (d) a hydrogen atom, a methyl group, an ethyl group, a hydroxyethyl group, and a hydroxypropyl group, (e) a substituent comprising a polyoxyalkylene group, (f) a sulfoalkyl group, (g) a carboxyalkyl group, and (h) a cationic substituent; Q identically or differently represents an alkylene group having 2 to 4 carbon atoms; a, b, and c identically or differently represent a number of 0 to 10; the QO groups, the R groups, or the numbers a, b, and c are identical or different in each repeating unit or between repeating units; and when each of the substituents (e) to (h) has a hydroxy group, the hydroxy group is optionally further substituted by any of other substituents (e) to (h), provided that at least one or more substituents (e) exist as R; and
(A-3) a polyether polycarbonate having a constitutional unit represented by formula (2):

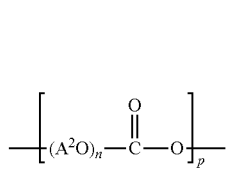

wherein $A^2$ represents an alkylene group having 2 to 6 carbon atoms; n represents a number of 5 to 1,000 on average; p represents a number of 5 to 100 on average; and A2, having a number of (n×p) units, are identical or different;
(B) 1 to 50% by mass of an oil agent comprising (b1) and (b2):
(b1) an ether oil and
(b2) a hydrocarbon oil having a viscosity of 18 mPas or lower at 30° C.; and
(C) water,
wherein the mass ratio of the total content of a fat in a paste or wax state at 30° C. to the content of said component (A) is 1/10 or less,
wherein said water is present in an amount of at least 65% by mass.

12. The cleansing composition according to claim 11, wherein component (A) is selected from the group consisting of an (acrylate/steareth-20 methacrylate) copolymer, an (acrylate/steareth-20 methacrylate) crosspolymer, and an (acrylate/beheneth-25 methacrylate) copolymer.

13. A skin cleansing composition comprising components (G), (H), (I), and (J):
(G) 0.001 to 5% by mass of a polymer selected from the group consisting of (G-1), (G-2), and (G-3):
(G-1) a copolymer comprising monomers selected from the group consisting of (g 1), (g2), and (g3) as constitutional units:
(g1) a monomer selected from the group consisting of acrylic acid and methacrylic acid,
(g2) a monomer selected from the group consisting of an acrylic acid alkyl ester and a methacrylic acid alkyl ester, and
(g3) a monomer selected from the group consisting of a polyoxyethylene alkyl ester of acrylic acid and a polyoxyethylene alkyl ester of methacrylic acid,
and comprising 10 mol % or more of the monomer unit (g2) based on the total monomers;
(G-2) a polysaccharide derivative having a polyoxyalkylene chain having an average molecular weight of 300 to 100,000 and having a constitutional unit represented by formula (1):

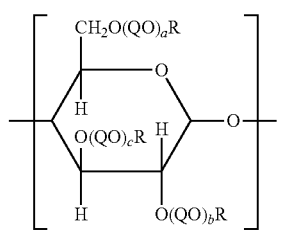

wherein R identically or differently represents a group selected from the group consisting of (d) a hydrogen atom, a methyl group, an ethyl group, a hydroxyethyl group, and a hydroxypropyl group, (e) a substituent comprising a polyoxyalkylene group, (f) a sulfoalkyl group, (g) a carboxyalkyl group, and (h) a cationic substituent; Q identically or differently represents an alkylene group having 2 to 4 carbon atoms; a, b, and c identically or differently represent a number of 0 to 10; the QO groups, the R groups, or the numbers a, b, and c are identical or different in each repeating unit or between repeating units; and when each of the substituents (e) to (h) has a hydroxy group, the hydroxy group is optionally further substituted by any of other substituents (e) to (h), provided that at least one or more substituents (e) exist as R; and (G-3) a polyether polycarbonate having a constitutional unit represented by formula (2):

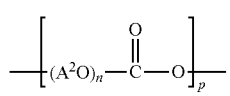

(2)

wherein $A^2$ represents an alkylene group having 2 to 6 carbon atoms; n represents a number of 5 to 1,000 on average; p represents a number of 5 to 100 on average; and $A^2$, having a number of (n×p) units, are identical or different;

(H) 0.001 to 1% by mass of a polymer comprising acrylic acid or methacrylic acid as a constituent, other than the component (G-1);

(I) 0.5 to 30% by mass of a hydrocarbon oil having a viscosity of 18 mPa·s or lower at 30° C.; and (J) 65 to 98% by mass of water, and comprising (K) no nonionic surfactant or 0.5% by mass or less of the nonionic surfactant, wherein the mass ratio between the components (G) and (H), (G)/(H) is 0.1 to 150, and the mass ratio of the total content of a fat in a paste or wax state at 30° C. to the content of said component (G) is 1/10 or less.

14. A method of cleansing skin, comprising applying a cleansing composition according to claim 1 to a face having a cosmetic composition thereon.

15. A method of cleansing skin, comprising wiping off a cosmetic present on a face with a cleansing composition according to claim 1.

16. A method of cleansing skin, comprising applying a skin cleansing composition according to claim 13 to a face having a cosmetic composition thereon.

17. A method of cleansing skin, comprising wiping off a cosmetic present on a face with a skin cleansing composition according to claim 13.

18. A cleansing composition according to claim 1, wherein the mass ratio of the total content of a fat in a paste or wax state at 30° C. to the content of said component (A) is 1/20 or less.

19. A cleansing composition according to claim 1, wherein the mass ratio of the total content of a fat in a paste or wax state at 30° C. to the content of said component (A) is 1/30 or less.

20. A cleansing composition according to claim 11, wherein the mass ratio of the total content of a fat in a paste or wax state at 30° C. to the content of said component (A) is 1/20 or less.

21. A cleansing composition according to claim 11, wherein the mass ratio of the total content of a fat in a paste or wax state at 30° C. to the content of said component (A) is 1/30 or less.

22. A skin cleansing composition according to claim 13, wherein the mass ratio of the total content of a fat in a paste or wax state at 30° C. to the content of said component (G) is 1/20 or less.

23. A skin cleansing composition according to claim 13, wherein the mass ratio of the total content of a fat in a paste or wax state at 30° C. to the content of said component (G) is 1/30 or less.

* * * * *